(12) United States Patent
Tajima

(10) Patent No.: US 10,656,111 B2
(45) Date of Patent: May 19, 2020

(54) DEVICE FOR ELECTRICAL MEASUREMENT OF TARGET CHEMICAL SUBSTANCE, AND METHOD THEREFOR

(71) Applicant: UNIVERSAL BIO RESEARCH Co., Ltd., Matsudo-shi, Chiba (JP)

(72) Inventor: Hideji Tajima, Matsudo (JP)

(73) Assignee: Universal Bio Research Co., Ltd. (JP)

( * ) Notice: Subject to any disclaimer, the term of this patent is extended or adjusted under 35 U.S.C. 154(b) by 126 days.

(21) Appl. No.: 15/742,700

(22) PCT Filed: Jul. 7, 2016

(86) PCT No.: PCT/JP2016/070097
§ 371 (c)(1),
(2) Date: Jan. 8, 2018

(87) PCT Pub. No.: WO2017/010392
PCT Pub. Date: Jan. 19, 2017

(65) Prior Publication Data
US 2018/0195986 A1    Jul. 12, 2018

(30) Foreign Application Priority Data

Jul. 10, 2015   (JP) .................................. 2015-139076

(51) Int. Cl.
*G01N 27/02*   (2006.01)
*G01N 27/27*   (2006.01)
(Continued)

(52) U.S. Cl.
CPC ............. *G01N 27/02* (2013.01); *G01N 27/27* (2013.01); *G01N 27/28* (2013.01); *G01N 35/10* (2013.01)

(58) Field of Classification Search
CPC ............. G01N 27/3272; G01N 27/327; G01N 27/3275; G01N 27/44791; G01N 15/1484;
(Continued)

(56) References Cited

U.S. PATENT DOCUMENTS 4,252,897 A  *  2/1981  Axford .................... C12Q 1/24
                                                                      435/286.3
4,680,270 A  *  7/1987  Mitsumaki ......... G01N 33/4915
                                                                      204/403.06
(Continued)

FOREIGN PATENT DOCUMENTS

JP     1986-165454     10/1986
JP     63-145164       9/1988
(Continued)

OTHER PUBLICATIONS

International Search Report (English translation) issued by the Japanese Patent Office regarding International Application No. PCT/JP2016/070097, dated Sep. 27, 2016, 2 pages.

(Continued)

*Primary Examiner* — Vinh P Nguyen
(74) *Attorney, Agent, or Firm* — Andrus Intellectual Property Law, LLP

(57) ABSTRACT

A device for electrical measurement of a target chemical substance includes: an electrode array element including a base, an electrode array section in which electrodes which are disposed on the base and to each of which a test substance is fixed or can be fixed are arrayed, and a terminal array section in which terminals disposed on the base so as to correspond to the electrodes and electrically connected to the electrodes are arrayed; a processing head having an electrode array element support section supporting the electrode array element detachably to make electrical connection to the terminals possible; a container group including a (Continued)

liquid storing section and a measurement container; a support section moving mechanism; and a measurement section capable of measuring a signal generated by applying a predetermined voltage to a test substance fixed to each of the electrodes in the measurement container.

9 Claims, 14 Drawing Sheets

(51) Int. Cl.
*G01N 27/28* (2006.01)
*G01N 35/10* (2006.01)

(58) Field of Classification Search
CPC .............. G01N 2015/149; G01N 21/77; G01N 2291/0255; G01N 27/26; G01N 29/036; G01N 33/487; G01N 33/48721; G01N 33/48728; G01N 2015/0065; G01N 2291/014; G01N 2333/9126; G01N 2458/30; G01N 27/3273; G01N 29/022; G01N 29/2437; G01N 33/48707; G01N 33/5011; G01N 27/02; G01N 27/27; G01N 27/28; G01N 35/10; G01N 27/4145; A61M 5/1723; A61M 2205/3327; A61M 5/172; A61B 18/1477; A61B 5/14546; A61B 2018/0072; A61B 2018/00767; A61B 2018/00875; A61B 2018/00982; A61B 2018/1425; A61B 2562/028; A61B 18/082; A61B 2018/00732; A61B 2018/00744; A61B 2018/00827; A61B 2018/00988; A61B 2018/1475; A61B 2562/227; A61B 5/145; A61B 5/14532; A61B 8/4427; A61B 90/98; A61B 18/14; A61B 18/1402; A61B 2017/00004; A61B 2018/00839; A61B 2018/00863; A61B 2018/00892; A61B 2560/063; A61B 2562/0217; A61B 2562/16; A61B 5/1468; A61B 5/6848; G01R 33/302; G01R 33/34007; G01R 33/341; G01R 33/448; G01R 33/3607; G01R 33/3621; G01R 33/3808; G01R 33/383
See application file for complete search history.

(56) References Cited

U.S. PATENT DOCUMENTS

| | | |
|---|---|---|
| 5,478,526 A | 12/1995 | Toshiba |
| 8,133,454 B2* | 3/2012 | Tajima ................ B01L 3/0275 |
| | | 422/501 |
| 2010/0170788 A1 | 7/2010 | Lin et al. |
| 2012/0318076 A1* | 12/2012 | Kappelhoff ........ G01N 35/0099 |
| | | 73/864.11 |

FOREIGN PATENT DOCUMENTS

| | | |
|---|---|---|
| JP | 10-146183 A | 6/1998 |
| JP | 2002055069 A | 2/2002 |
| JP | 2004177151 A | 6/2004 |
| JP | 2008145441 A | 6/2008 |
| JP | 2008157956 A | 7/2008 |
| JP | 2010160151 A | 7/2010 |

OTHER PUBLICATIONS

International Search Report and Written Opinion issued by the Japanese Patent Office regarding International Application No. PCT/JP2016/070097, dated Sep. 27, 2016, 7 pages.
International Preliminary Report on Patentability issued by the Japanese Patent Office regarding International Application No. PCT/JP2016/070097 dated Jul. 21, 2017, 11 pages.

* cited by examiner

DEVICE FOR ELECTRICAL MEASUREMENT OF TARGET CHEMICAL SUBSTANCE, AND METHOD THEREFOR

CROSS REFERENCE

This application is a United States national phase application of co-pending international patent application number PCT/JP2016/070097, filed Jul. 7, 2016, which claims priority to Japanese patent application number 2015-139076, filed Jul. 10, 2015, the entire disclosures of which are hereby incorporated herein by reference.

TECHNICAL FIELD

The present invention relates to a device for electrical measurement of a target chemical substance for performing electrical measurement of a target chemical substance contained in a sample, and a method therefor.

BACKGROUND ART

In recent years, a target biological substance to be tested (an example of a target chemical substance) is extracted from a specimen collected from a subject or the like, the target biological substance thus extracted is labeled with a fluorescent substance or a chemiluminescent substance, a solution containing the target biological substance is caused to come into contact with a carrier such as a DNA chip or a string-shaped probe array by fixing a plurality of kinds of test substances (probes) having a predetermined relationship with the target biological substance at a predetermined plurality of different positions which can be distinguished from an outside in a planar shape or one-dimensional manner, or the solution containing the target biological substance is stored in a well of a microplate which stores the test substance or to which the test substance is fixed to cause a reaction, and the target biological substance is tested based on presence or absence of fluorescence or chemiluminescence at each position on the carrier or in each well.

In measurement of fluorescence and chemiluminescence, it is necessary to label a target biological substance with a fluorescent substance or a chemiluminescent substance in advance, and then to guide light from a container where a reaction takes place to a light receiving section using an optical system such as an optical fiber. Furthermore, a carrier such as a DNA chip or a string-shaped probe array needs to be arrayed so as to be measurable from an outside of a translucent dispensing tip. Processing may require labor, or a device scale may expand.

Meanwhile, in place of performing optical measurement, there is a detecting device for determining presence or absence of a target biological substance and a base structure of the target biological substance by disposing a sensor having arrayed therein electrodes to which test substances capable of bonding to the target biological substance are fixed (Patent Literature 1).

In the device, processing is performed by disposing the sensor in a holder and moving a reaction tank, a cleaning tank, an intercalating agent solution tank, and a measuring tank, or by attaching the sensor to an inside of a container and dispensing or removing a required reagent.

Alternatively, the sensor is incorporated in a micro liquid circuit, a sample is introduced by a hand method, and voltage is applied to perform measurement.

CITATION LIST

Patent Literature

Patent Literature 1: JP 2008-145441 A
Patent Literature 2: JP 2008-157956 A
Patent Literature 3: JP 10-146183 A

SUMMARY OF INVENTION

Technical Problem

However, depending on contents to be detected, if the number of electrodes increases or the number of electrodes to be arrayed on the sensor increases, in order to perform processing by moving the sensor and immersing the sensor in a reaction tank, a cleaning tank, and a measuring tank, a sufficient amount of liquid is necessary and it is necessary to dispose a storing container having a large capacity to store the sufficient liquid amount, and a sample may be diluted. Furthermore, it may be impossible to sufficiently enhance encounterability and reactivity between a target chemical substance and a test substance on an electrode.

Furthermore, it is not easy in terms of manufacturing to dispose a plurality of electrodes at an inner bottom of a container so as to be able to come into contact with liquid, and to dispose a plurality of terminals electrically connected to the electrodes on an outer surface of the container so as not to be able to come into contact with the liquid. Even if such a structure can be manufactured, it may be difficult to reliably fix a test substance to a plurality of electrodes or to efficiently clean the plurality of electrodes. In addition, also in a case where an electrode or a sensor is disposed at a bottom of a container and a relatively small amount of reaction liquid or cleaning liquid is exchanged for use, it may be impossible to enhance encounterability and reactivity between a target chemical substance and a test substance on the electrode sufficiently.

Attaching an electrode or a sensor to a moving mechanism by a hand method, dispensing microfluidized liquid to the sensor incorporated in a micro liquid circuit by a hand method, or attaching the sensor to a holder has a risk of not only increase in a burden of a user but also contamination of a user by the liquid or occurrence of cross contamination. Furthermore, in recent years, an electrode or a base having electrodes arrayed thereon is formed easily and inexpensively in a film shape. Therefore, utilization thereof is preferable.

Therefore, the present invention has been achieved in order to solve the above problems. A first object of the present invention is to provide a simple and inexpensive device for electrical measurement of a target chemical substance by preventing increase in a device size and complication of processing by utilizing a mechanism originally included in extraction reaction processing of a target chemical substance without using an optical part or device for measuring presence or absence of a target chemical substance, a structure thereof, or the like, and a method therefor. A second object of the present invention is to provide a device for electrical measurement of a target chemical substance, capable of performing processing efficiently and rapidly by further enhancing encounterability and reactivity not only for processing such as fixation of a test substance to an electrode or cleaning but also for reaction processing in measurement processing using an electrode, and a method therefor. A third object of the present invention is to provide a device for electrical measurement of a target chemical substance, causing no cross contamination by consistently automating processing including measurement, easily handled by reducing user's labor, and having high reliability, and a method therefor.

Solution to Problem

A first invention is a device for electrical measurement of a target chemical substance, including: one or more electrode array elements each including a base, an electrode array section in which one or more electrodes which are disposed on the base and to each of which a test substance having a bonding property to a target chemical substance is fixed or can be fixed are arrayed, and a terminal array section in which one or more terminals disposed on the base so as to correspond to the electrodes and electrically connected to the electrodes are arrayed; a processing head including one or more electrode array element support sections supporting the electrode array elements detachably to make electrical connection to the terminals in the terminal array section possible; a container group including one or more liquid storing sections capable of storing liquid, and one or more measurement containers; a support section moving mechanism capable of relatively moving the one or more electrode array element support sections with respect to the container group; and a measurement section capable of measuring a signal generated by applying a predetermined voltage to a test substance fixed to each of the electrodes in the measurement containers, in which the container group includes one or more electrode array element storing sections storing or capable of storing the electrode array elements such that the electrode array elements can be supported by the electrode array element support sections due to the support section moving mechanism.

Here, the "target chemical substance" includes, for example, a genetic substance such as a nucleic acid, and a biochemical substance including a biopolymer such as a protein, a sugar, a sugar chain, or a peptide, and a low molecular substance. The "test substance" is a biochemical substance as a receptor having a bonding property to the target chemical substance as a ligand, and is used for bonding to, capturing, separating, and extracting the target chemical substance. A genetic substance as the target chemical substance, such as a nucleic acid, a genetic substance having a bonding property to a protein, a sugar chain, a peptide, or the like, such as a nucleic acid, and a biological substance such as a protein, a sugar chain, or a peptide correspond to the receptor. For the target chemical substance or the test substance, a living body itself such as a cell, a virus, or a plasmid can be used as a biological substance or in place of the biological substance. The target substance is present in a solution stored in the liquid storing section of the container group.

"Fixing" means associating at least one of the chemical substances with the electrode directly or indirectly through a different kind of substance. Examples of bonding include physical adsorption, hydrogen bonding, and bonding by electrical interaction in addition to covalent bonding and bonding by chemical adsorption. Alternatively, fixing is performed by a specific reaction between a test substance possessed by the electrode and various substances or by another method.

For example, the "electrode array element" has an opening in a part of an insulator covering a conductor (including an electrode, a terminal, and a conductive wire) disposed on a base such that the conductor is exposed, and fixes or makes it possible to fix the test substance to an electrode using the conductor exposed from the opening as the electrode. Here, examples of the base include an inorganic insulator such as glass, alumina, sapphire, silica, silicon carbide, or another metal oxide, and an organic insulator such as polyethylene, polypropylene, or ethylene. Examples of the conductor include a metal simple substance such as gold, an alloy thereof, and graphite. The electrode is electrically connected to a terminal by the covered conductor. The "base" is not necessarily limited to a plate shape, but may include a dispensing element as described below. In a case where the "electrode array element support section" supports the electrode array element by fitting the terminal array section of the electrode array element with a plug or in a case where a base includes a dispensing element, the electrode array element support section supports the electrode array element by attaching an attachment opening of the dispensing element to a nozzle, and the terminal array section may come into contact with a connection terminal or a conductive section of a plug, or the electrode array element support section supports the electrode array element by holding a deformable dispensing element, and the terminal array section may come into contact with the connection terminal or the conductive section of the plug. Note that it is necessary that the electrode array element support section is supported such that each electrode arrayed in the electrode array section can come into contact with liquid stored in the liquid storing section and the measurement container but cannot come into contact with the terminals, or movement of the electrode array element support section is controlled by the support section moving mechanism in such a manner.

The "measurement container" is a container including an antipole (or counter electrode) corresponding to an electrode such that a predetermined voltage can be applied to a test substance fixed to the electrode in a solution. For example, an antipole with respect to an electrode to which a test substance of the electrode is fixed is disposed, and a voltage is applied between the electrode and the antipole such that the measurement section applies a voltage to the test substance fixed to the electrode. A signal generated by the applied voltage includes an electric signal such as a current value, electric conductivity, a potential, a resistance value, electric capacitance, inductance, or impedance. By measuring the signal, it is possible to detect presence or absence and the amount of a test substance present in the electrode and a bonded target chemical substance. In order to obtain an electric signal, for example, a target chemical substance such as a nucleic acid is labeled by an electrochemically active substance such as Hoechst 33258, acridine orange, quinacrine, daunomycin, an intercalating agent such as a metallo-intercalator, a bis-intercalator such as bisacridine, a tris-intercalator, or a poly-intercalator, a phyllocene, or a metal complex due to hybridization between the target chemical substance and a test substance fixed to an electrode, such as a nucleic acid, an electric signal such as a reaction current value derived from the electrochemically active substance is detected by applying a voltage, and the amount of the target chemical substance which has reacted with the test substance such as a nucleic acid can be detected. Furthermore, for detection of a target chemical substance using an antigen-antibody reaction, an antigen of the target chemical substance may be labeled with these substances in advance. Incidentally, in labeling, the concentration of an intercalating agent, an enzyme, or the like varies depending on the kind thereof, but the concentration is generally in a range of 1 ng/mL to 1 mg/mL. At this time, a buffer solution having an ionic strength of 0.01 to 5 and a pH of 5 to 10 is preferably used. In addition, it may be possible to measure presence or absence and the amount of a target chemical substance bonded to a test substance of an electrode by measuring impedance or the like without particularly performing labeling. For example, by applying an alternating voltage, bonding or adsorption of a target chemical substance or the like to an electrode surface changes capacitor capacitance of an electrode double layer, and as a result, an impedance value changes. Therefore, by measuring the impedance value, presence or absence and the amount of a target chemical substance can be measured.

Note that one of the electrodes arrayed in the electrode array element may be a reference electrode with a ground as a reference system. At this time, electrical measurement is performed with a three electrode type (reference electrode, antipole, and electrode), or two electrode type (antipole and electrode), and a current value or the like derived from an intercalating agent or the like is measured. For measurement, a current and a voltage are controlled using a device such as a potentiostat, a digital multimeter, or a function generator. The concentration of a target chemical substance bonded to a test substance is calculated from a calibration curve based on the obtained current value or the like. The "processing head" is preferably disposed so as to be relatively movable with respect to the container group. In a case where a processing head moving mechanism for moving the processing head with respect to the container group is disposed, the processing head moving mechanism constitutes, for example, a part of the support section moving mechanism. For example, the processing head moving mechanism is a mechanism for moving a processing head in a horizontal direction (for example, an X-axis direction or a Y-axis direction) relatively with respect to the container group. The support section moving mechanism includes a Z-axis moving mechanism disposed in a processing head and moving the electrode array element support section in a Z-axis direction with respect to the processing head in addition to the processing head moving mechanism. Here, the term "relative" indicates that a relative relation is satisfied in a relation to another object to be compared. Therefore, a case of "relatively moving" includes a case where one of objects (for example, electrode array element support section) moves and the other of the objects (for example, container group) is stationary, a case where one of objects is stationary and the other of the objects moves, and a case where both objects move (a case where the objects move at different speeds).

A second invention is a device for electrical measurement of a target chemical substance, in which the base is formed in a plate shape having a predetermined height, a predetermined width, and a predetermined thickness shorter than the predetermined height and the predetermined width, the electrode array element support section includes a plug detachably attached to the terminal array section formed on an upper side of the base and electrically connectable to the terminals of the terminal array section, and the container group includes a liquid storing section or a measurement container having an inner width longer than the predetermined width of the base and an inner depth longer than the predetermined thickness but shorter than the predetermined width.

Here, the "plug" includes one or more connection terminals attached to the terminal array section and electrically connectable to the terminals arrayed in the terminal array section. The base is, for example, a thin rectangular parallelepiped. The electrode array element can make electrode array surface come into contact even with a small amount of liquid, and can prevent a decrease in encounterability due to dilution of the liquid. A normal direction of the electrode array surface of the electrode array element can be moved in a fixed direction all the time. A moving operation including automatic attachment to the plug is easy.

A third invention is a device for electrical measurement of a target chemical substance, in which the processing head further includes a suction and discharge mechanism for sucking and discharging gas, and the electrode array element support section includes: a dispensing element support section detachably supporting a dispensing element capable of sucking and discharging liquid through a mouth portion at a lower end due to the suction and discharge mechanism; and a plug detachably attached to the terminal array section of the electrode array elements and electrically connected to the terminals.

Here, the "dispensing element" is an instrument capable of sucking and discharging liquid, for example, a dispensing tip attached to a nozzle communicating with a gas suction and discharge mechanism, or a deformable dispensing tip which can be deformed by a movable member. In a case where the dispensing element is a dispensing tip, the dispensing element support section includes a nozzle communicating with a suction and discharge mechanism for sucking and discharging gas. In a case where the dispensing element is a deformable dispensing tip, the suction and discharge mechanism includes a movable member for deforming the deformable dispensing tip, and the dispensing element support section includes a member for supporting the deformable dispensing tip such that a tip end of the deformable dispensing tip does not fluctuate.

In a case where the dispensing element is detachably supported, the container group preferably includes a dispensing element storing section for storing at least the dispensing element such that the dispensing element is supported by the processing head due to array element moving mechanism. In a case where the electrode array element support section includes a nozzle communicating with the suction and discharge mechanism for sucking and discharging gas, the dispensing element is a dispensing tip detachably attached to the nozzle through an attachment opening at an upper end thereof.

Here, the dispensing element is not limited to a case where the electrode array section is disposed inside (including a case of "a base of an electrode array element" described below), but includes a case of normal use of a dispensing tip with no electrode array section disposed inside. In a case where the electrode array section is disposed in the dispensing element, contact between the electrode and liquid can be accelerated by repeating suction and discharge of the liquid.

A fourth invention is a device for electrical measurement of a target chemical substance, in which the base of the electrode array element includes the dispensing element, the electrode array section is disposed inside the dispensing element, and the terminal array section is disposed inside the dispensing element so as to be located above the electrode array section or is disposed outside the dispensing element.

For example, the electrode array element is obtained by rounding a rectangular sheet-shaped electrode array element having an electrode array section disposed on a lower side and having a terminal array section disposed on an upper side into a cylindrical shape with a vertical direction as an axis, and connecting both edges of the cylindrical shape to each other without a gap to form a tube such that an upper portion of the tube is attachable to a nozzle communicating with the suction and discharge mechanism. In this case, by disposing a filter through which only gas passes so as to make a partition between the electrode array section and the terminal array section in the tube, contact between liquid sucked into the tube on a lower side of the filter and the terminal array section can be avoided. A plug with a conductive section electrically connectable to each terminal of the terminal array section is disposed in the nozzle to be attached when the nozzle is attached. Alternatively, for example, by bonding the film-shaped electrode array element to an inner wall of a rigid cylindrical tube such that the electrode array section can come into contact with liquid, the base of the electrode array element may be formed into a tubular shape. Alternatively, a plate-shaped electrode array element may be formed so as to penetrate a side surface of a dispensing element such that an electrode array section and a terminal array section are disposed inside and outside the dispensing element, respectively. According to the present invention, the electrode array section can come into contact with liquid efficiently and reliably, and contact between the terminal array section and the liquid can be prevented reliably.

A fifth invention is a device for electrical measurement of a target chemical substance, in which the dispensing element is a dispensing tip, the dispensing element support section includes a nozzle communicating with a suction and discharge mechanism for sucking and discharging gas, the dispensing tip is supported by being detachably attached to the nozzle through an attachment opening at an upper end thereof, the plug is disposed at a tip end of the nozzle such that the electrode array element is located inside the dispensing tip, and the container group further includes a tip storing section for storing the dispensing tip such that the dispensing tip is attachable to the nozzle.

Here, as described below, the dispensing tip preferably includes at least a thick tube and a thin tube, and the electrode array section is preferably disposed in the thick tube. In this case, dispensing of a sample or a necessary reagent into a liquid storing section, extraction of a nucleic acid using magnetic particles, or the like can be performed consistently using a dispensing tip having no electrode array element disposed. The nozzle preferably includes a detachment mechanism for detaching the dispensing tip or the electrode array element from the nozzle. Furthermore, the nozzle includes a plug electrically connectable to each terminal of the terminal array section of the electrode array element. An opening of the liquid storing section of a reagent is preferably covered with a thin film such as an aluminum film in advance such that the thin film can be pierced. A piercing tip for piercing the thin film is preferably attached to the nozzle so as to be able to pierce the thin film.

Note that the dispensing tip is attached to the nozzle such that the electrode array section is located in the dispensing tip after the electrode array element is attached to the nozzle.

A sixth invention is a device for electrical measurement of a target chemical substance, in which the dispensing element includes a thin tube having the mouth portion, a thick tube communicating with the thin tube, and a storage tube communicating with the thick tube, the electrode array section is disposed in the thick tube, and the storage tube is disposed so as to have a capacity capable of storing all the liquid introduced into the thick tube from the mouth portion.

Here, in a case where the dispensing element is a dispensing tip, the dispensing tip has an attachment opening at an upper end of the storage tube, and the attachment opening is detachably attached to the nozzle communicating with the suction and discharge mechanism to be used. The storage tube means a part above the thick tube part where the electrode array section is disposed. Note that the thickness or capacity of a tube of the tip is preferably increased in order of the thin tube, the thick tube, and the storage tube.

A seventh invention is a device for electrical measurement of a target chemical substance, including a vibration mechanism for vibrating the electrode array element support section or the electrode array element.

Here, the "vibration mechanism" includes an ultrasonic vibrator, a vibration motor, and the like. Particularly, in a case where the electrode array element support section or the electrode array element is vibrated, a molded member such as plastic is partially used. Therefore, an arm for preventing fall of the electrode array element or the like is preferably disposed by utilizing a protruding portion formed on a base of the electrode array element. The arm can also have a vibration function.

An eighth invention is a device for electrical measurement of a target chemical substance, in which two non-wetted electrodes for application of an external electric field are disposed in the measurement containers or the liquid storing sections so as to sandwich an inside of the measurement container or an inside of the liquid storing section such that an electric field can be externally applied to the inside of the measurement container or the liquid storing section while the non-wetted electrodes are not in contact with liquid stored in the measurement container or the liquid storing section.

By applying an external electric field to an inside of the measurement container, molecular motion (Brownian motion) is activated with respect to a solution stored in the measurement container. A stirring effect of the solution is thereby enhanced, encounterability between a test substance fixed to an electrode disposed on the electrode array element and a target chemical substance is enhanced, and measurement with high reliability can be performed. In this case, it is effective to generate an electric field having a magnitude and a direction changing with time by applying an alternating current to the electrode. In this case, an alternating voltage to be applied is 1 to 10 kV, a distance between the electrodes is 2 to 10 mm, and a frequency is 10 to 100 Hz. In order to dispose the electrodes so as to be in a non-wetted state, for example, the electrodes are disposed outside a side wall of the measurement container or the liquid storing section or in a wall thickness of the side wall.

A ninth invention is a device for electrical measurement of a target chemical substance, in which the processing head includes a magnetic force mechanism capable of applying a magnetic force to an inside of the attached dispensing element and removing the magnetic force therefrom and/or a temperature raising and lowering body for raising and lowering a temperature according to a signal from an outside, disposed so as to be close to or be able to approach an outside of the dispensing element or the electrode array element attached to the processing head, and the magnetic force mechanism and/or the temperature raising and lowering body are controlled by control section. Here, "close" and "approach" may also include a case of being in contact.

A tenth invention is a method for electrical measurement of a target chemical substance, including: an electrical connection step of relatively moving one or more electrode array element support sections with respect to a container group including one or more electrode array element storing sections for storing one or more electrode array elements each including a base, an electrode array section in which one or more electrodes which are disposed on the base and to each of which a test substance having a bonding property to a target chemical substance is fixed are arrayed, and a terminal array section in which one or more terminals disposed on the base so as to correspond to the electrodes and electrically connected to the electrodes are arrayed, one or more liquid storing sections for storing liquid, and one or more measurement containers, and causing the electrode array element support sections disposed in a processing head to support the electrode array elements detachably for electrical connection to the terminals; a liquid contact step of relatively moving the electrode array element support sections with respect to the container group, and thereby inserting the electrodes into the one or more liquid storing sections such that the electrodes come into contact with liquid; and a measurement step of relatively moving the electrode array element support sections with respect to the container group, thereby inserting the electrodes into the one or more measurement containers, applying a predetermined voltage to a test substance fixed to each of the electrodes, and measuring a signal generated thereby.

An eleventh invention is a method for electrical measurement of a target chemical substance, in which the base is formed in a plate shape having a predetermined height, a predetermined width, and a predetermined thickness shorter than the predetermined height and the predetermined width, the electrode array element support section includes a plug detachably attached to the terminal array section and electrically connected to the terminals, the electrical connection step is performed by relatively moving the electrode array element support section above the electrode array element storing section storing the electrode array element, and lowering the plug such that the terminal array section formed on an upper side of the base is detachably attached to the plug, and the liquid contact step is performed by inserting the electrodes into a liquid storing section having a longer inner width than the predetermined width of the base and an inner depth longer than the predetermined thickness but shorter than the predetermined width.

A twelfth invention is a method for electrical measurement of a target chemical substance, in which the processing head further includes a suction and discharge mechanism for sucking and discharging gas, the electrode array element support section includes a dispensing element support section detachably supporting a dispensing element capable of sucking and discharging liquid due to the suction and discharge mechanism, and a plug detachably attached to the terminal array section and electrically connected to the terminals, the electrical connection step includes at least a step of relatively moving the electrode array element support sections with respect to the container group, and thereby detachably attaching the terminal array section of the electrode array element to the plug for electrical connection to the terminals, and the method further includes a step of causing the dispensing element support section of the electrode array element support section to detachably support a dispensing element capable of sucking and discharging liquid due to the suction and discharge mechanism during, before, or after the electrical connection step.

Here, the dispensing element includes a (cylinder type) dispensing tip and a deformable dispensing tip. In a case of the dispensing tip, a dispensing element support section is a nozzle communicating with the suction and discharge mechanism. A case where attaching of the terminal array section to the plug and attaching thereof to the dispensing element support section are performed at the same time is also included.

A thirteenth invention is a method for electrical measurement of a target chemical substance, in which the base of the electrode array element includes the dispensing element, the electrode array section is disposed inside the dispensing element, and the terminal array section is disposed inside the dispensing element so as to be located above the electrode array section or is disposed outside the dispensing element, and the method includes a step of causing the dispensing element support section to support the dispensing element, and a step of detachably attaching the terminal array section of the electrode array element to the plug for electrical connection to the terminals, during the electrical connection step.

A fourteenth invention is a method for electrical measurement of a target chemical substance, in which the electrode array element support section includes a nozzle communicating with the suction and discharge mechanism as a dispensing element support section capable of sucking and discharging liquid due to the suction and discharge mechanism and detachably supporting a dispensing tip, and a plug disposed at a lower end of the nozzle, detachably attached to the terminal array section, and electrically connected to the terminals, the electrical connection step is performed by relatively moving the nozzle as the electrode array element support section with respect to the electrode array element storing section storing the electrode array element, lowering the nozzle, thereby detachably attaching the terminal array section to the plug disposed at a lower end of the nozzle for electrical connection to the terminals, relatively moving the nozzle with respect to the tip storing section storing the dispensing tip, lowering the nozzle, and thereby attaching the dispensing tip to the nozzle attached to the electrode array element so as to store the electrode array element inside thereof, and the liquid contact step is performed by relatively moving the attached dispensing tip with respect to the container group, inserting the dispensing tip into the liquid storing section, causing the nozzle to suck and discharge liquid, and thereby causing the electrodes to come into contact with the liquid.

A fifteenth invention is a method for electrical measurement of a target chemical substance, in which the electrical connection step is performed by relatively moving the nozzle as the electrode array element support section with respect to the electrode array element storing section storing the electrode array element, lowering the nozzle, thereby attaching the nozzle to an attachment opening of a dispensing tip included in the electrode array element, and detachably attaching the plug to a terminal array section of the electrode array element, and the liquid contact step is performed by relatively moving the attached dispensing tip of the electrode array element with respect to the container group, inserting a lower end of the dispensing tip into the liquid storing section, causing the dispensing tip to suck and discharge liquid, and thereby causing the electrode to come into contact with the liquid.

A sixteenth invention is a method for electrical measurement of a target chemical substance, in which the liquid contact step includes a step of vibrating the electrode array element support section.

A seventeenth invention is a method for electrical measurement of a target chemical substance, in which the liquid contact step includes a step of application of an external electric field for applying an external electric field to the liquid storing section or the measurement container using a non-wetted electrode.

Here, the size and direction of the external electric field preferably fluctuate with time in order to activate molecular motion.

An eighteenth invention is a method for electrical measurement of a target chemical substance, further including a step of applying a magnetic force to an inside of a dispensing element supported by the processing head and removing the magnetic force therefrom due to a magnetic force mechanism, or a step of raising and lowering a temperature of a temperature raising and lowering body disposed so as to be close to or be able to approach an outside of the dispensing element or the electrode array element supported by the processing head according to a signal from an outside.

A nineteenth invention is an electrode array element including: a base including a dispensing element having a mouth portion for sucking and discharging liquid at a lower end thereof; an electrode array section in which one or more electrodes which are disposed inside the dispensing element and to each of which a test substance having a bonding property to a target chemical substance is fixed or can be fixed are arrayed; and a terminal array section in which one or more terminals electrically connected to the electrodes so as to correspond to the electrodes are arrayed, in which the terminal array section is disposed inside the dispensing element so as to be located above the electrode array section or is disposed outside the dispensing element.

In a case where the dispensing element is a (cylinder type) dispensing tip, an attachment opening attachable to a nozzle communicating with a suction and discharge mechanism for sucking and discharging gas is formed at an upper end of the dispensing tip. The mouth portion of the dispensing element is formed so as to be able to be inserted into a container such as a liquid storing section or a measurement container of a container group.

Advantageous Effects of Invention

According to the first or tenth invention, the electrode array element is stored in the electrode array element storing section such that the electrode array element can be supported by the electrode array element support section, and the electrode array element support section is relatively movable with respect to the container group. As a result, by automatically performing support of the electrode array element by the electrode array element support section and electrical connection, it is possible to prevent contamination by a user against the electrode array element or contamination to the user, and to perform processing and measurement with high reliability.

It is unnecessary to include a light measurement device. By preparing a reagent necessary for a container group and a sample and moving the electrode array element support section between storing sections or with respect to a measurement container, processing from sample processing to measurement can be performed consistently and efficiently. Therefore, a small, inexpensive, simple, and highly accurate device can be provided. Therefore, shortening of test time (POCT) in medical care and clinical diagnosis can be realized, and a test can be performed next to a patient. Such a device is particularly useful for an on-site test of foods, allergens, and the like.

According to the second or eleventh invention, a base of the electrode array element is formed into a thin plate shape, and a container into which the electrode array element is inserted is made thin in accordance with the electrode array element. It is thereby possible to reliably bring even a small amount of sample solution into contact with an electrode of the electrode array element. Therefore, encounterability can be enhanced without diluting the sample solution.

Use of a thin electrode array element makes it possible to easily cause the electrode array element support section to support the electrode array element. It is possible to provide a device with a simple structure by preventing an overall scale of the device from being expanded.

According to the third or twelfth invention, by disposing the suction and discharge mechanism for sucking and discharging gas and the electrode array element support section including the dispensing element support section and the plug in the processing head, not only the electrode array element but also the dispensing element is movable with respect to the container group, liquid in each liquid storing section is transferred, and consistent automatic processing can be performed. In addition, contact between the electrode and the liquid can be accelerated by using each dispensing element, and encounterability between a target chemical substance and a test substance can be enhanced and a reaction can be accelerated by repeating suction and discharge of the liquid.

According to the fourth, thirteenth, or nineteenth invention, by incorporating the dispensing element into the base as the electrode array element, in addition to the above effect, contact between liquid and an electrode can be performed efficiently and reliably. However, by reliably eliminating contact between the liquid and a terminal, processing with high reliability can be performed. In addition, the dispensing element can be easily incorporated by processing a sheet-shaped or film-shaped electrode array element. It is possible to perform attachment of the dispensing element and support as the electrode array element at the same time, and rapid processing can be performed.

According to the fifth or fourteenth invention, the nozzle as the electrode array element support section is relatively moved using an array element moving mechanism, the dispensing tip is attached to the nozzle after the electrode array element is attached to the nozzle, and the electrode array element is stored in the dispensing tip to be used. Therefore, as compared with a case where an electrode of an electrode array element is simply brought into contact with liquid in each storing section, by repeatedly sucking and discharging liquid by the dispensing tip, it is possible to enhance encounterability between a target substance and a test substance fixed to an electrode in the liquid, to accelerate a reaction, and to speed up processing. In addition, even in a case where cleaning is performed, it is possible to reliably perform cleaning by repeating suction and discharge. Furthermore, the dispensing tip can be used not only for measurement processing but also for dispensing processing to each liquid storing section, and is highly versatile and efficient.

According to the sixth invention, all the liquid introduced from the thin tube to the thick tube where the electrode array section is located can be introduced into a storage tube capable of storage, and therefore it is possible to bring all the liquid introduced into contact with the electrode array section, and encounterability can be enhanced.

According to the seventh or sixteenth invention, by vibrating the electrode array element support section or the electrode array element while the electrode array element is immersed in liquid stored in the measurement container, encounterability between a target chemical substance and a test substance fixed to the electrode in the liquid is enhanced, and a reaction is accelerated. As a result, processing or measurement time can be shortened, and the processing can be performed rapidly.

According to the eighth or seventeenth invention, by applying an external electric field to an inside of the liquid storing section or the measurement container, while an electrode does not come into contact with liquid in which the electrode array element is immersed and which is stored in the liquid storing section or the measurement container, the liquid is stirred, encounterability between a target substance and a test substance fixed to the electrode in the solution can be enhanced, and bonding can be accelerated. Therefore, it is possible to avoid new contact between a solution and a component by stirring, to prevent contamination based on scattering of the solution by stirring, to accelerate a reaction, to shorten processing time, and to perform processing with high reliability.

According to the ninth or eighteenth invention, the temperature raising and lowering body disposed so as to be close to or be able to approach a dispensing element controls temperature inside the dispensing element, and it is possible to accelerate a reaction between a target substance and a test substance fixed to a porous stationary phase carrier in mobile phase solvent. Therefore, reaction time can be shortened, and highly efficient processing can be performed. Furthermore, by disposing the magnetic force mechanism, a target substance is separated from a sample using magnetic particles, and it is thereby possible to consistently perform processing from extraction to measurement with a single device. Therefore, efficiency is high.

DESCRIPTION OF EMBODIMENTS

Subsequently, a device for electrical measurement of a target chemical substance 10 according to an embodiment of the present invention will be described with reference to FIGS. 1 to 6.

Figure 1:
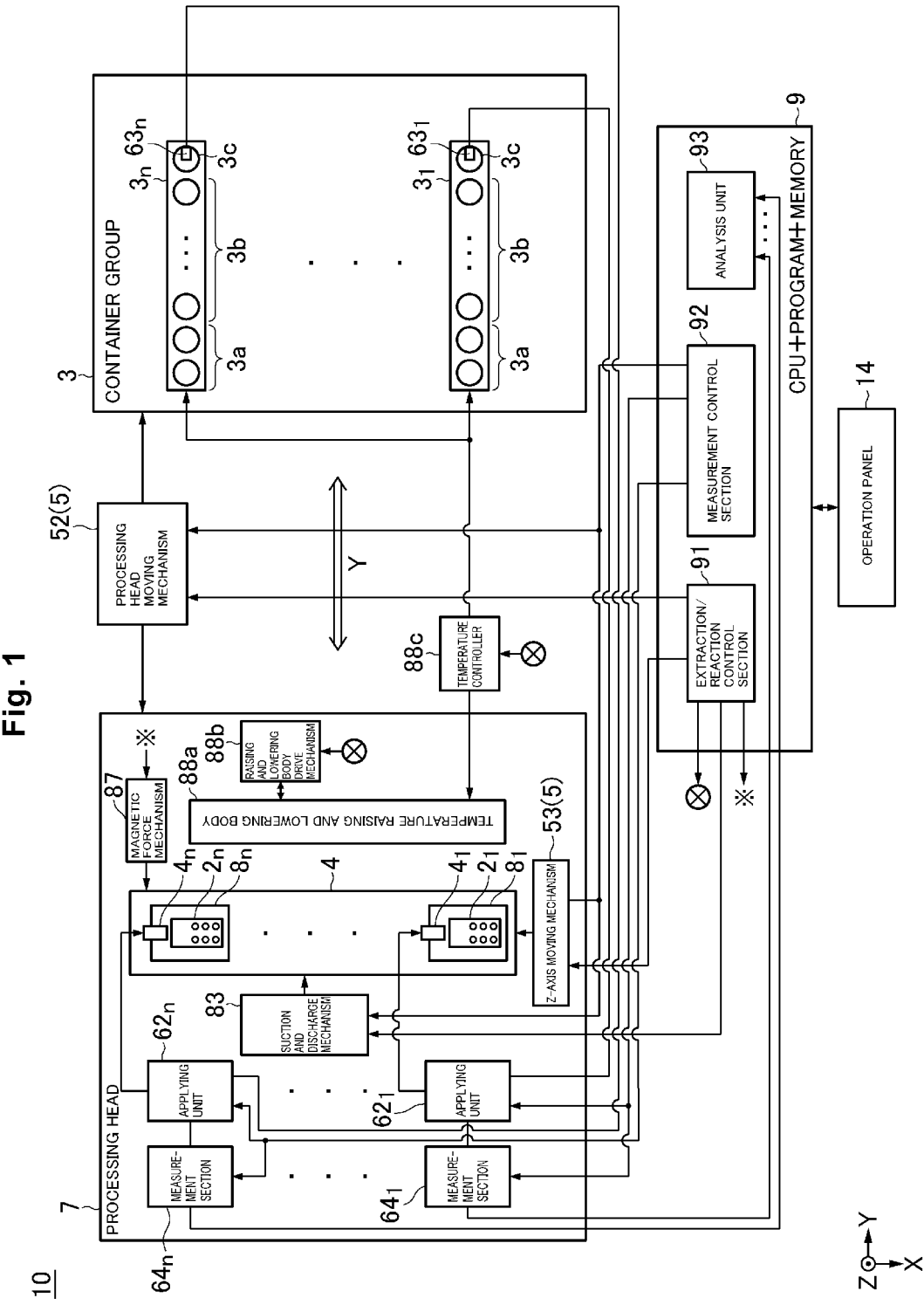
FIG. 1 is a block diagram illustrating a device for electrical measurement of a target chemical substance according to an embodiment of the present invention.

FIG. 1 is a block diagram illustrating the device for electrical measurement 10.

The device for electrical measurement 10 roughly includes: for example, a container group 3 including storing section groups $3_1$ to $3_n$ ("n" is equal to the number of the electrode array elements) in which a plurality of storing sections storing various solutions, an electrode array element described below, and various dispensing tips, arrayed in a row in a Y-axis direction is arrayed inn rows in an X-axis direction on a stage; a processing head 7 disposed so as to be movable in a relatively horizontal direction with respect to the container group 3, for example, in the Y-axis direction, and including electrode array element support sections $4_1$ to $4_n$ which can sequentially selectively support either one or more (n in this example) electrode array elements $2_1$ to $2_n$ or dispensing elements $8_1$ to $8_n$ a tip end portion of which can be inserted into each of the storing sections, or can support both thereof overlappingly; a support section moving mechanism 5 for making the electrode array element support sections $4_1$ to $4_n$ disposed in the processing head 7 relatively movable with respect to the container group 3; a CPU+program+memory 9 for performing information processing for various kinds of control; and an operation panel 14 for performing operation such as an instruction of a user to the CPU+program+memory 9. Examples of the various solutions include a sample solution which can contain a target chemical substance, a solution of an intercalating agent or an electrically active substance, a detergent, a buffer solution, a dissociated solution, a solution for extraction, a solution for PCR, and other various reagents.

The processing head 7 further includes an array element support 4 in which one or more electrode array element support sections $4_1$ to $4_n$ which sequentially selectively support either the electrode array elements $2_1$ to $2_n$ or the dispensing elements $8_1$ to $8_n$ or support both thereof overlappingly are arrayed at a predetermined pitch; a suction and discharge mechanism 83 for sucking and discharging gas with respect to the dispensing elements $8_1$ to $8_n$; applying units $62_1$ to $62_n$ for applying a predetermined voltage to a test substance fixed to an electrode disposed in each of the electrode array elements $2_1$ to $2_n$; and measurement sections $64_1$ to $64_n$ capable of measuring an electric signal from the electrode generated by applying the predetermined voltage to the test substance.

Each of the storing section groups $3_1$ to $3_n$ of the container group 3 at least includes: a tip and the like storing section group 3a storing the dispensing elements $8_1$ to $8_n$ and the electrode array elements $2_1$ to $2_n$ such that the dispensing elements $8_1$ to $8_n$ and the electrode array elements $2_1$ to $2_n$ can be supported by the electrode array element support sections $4_1$ to $4_n$; a liquid storing section group $3b$ storing various liquids; and a measurement container $3c$ for measuring the electrode array elements, including antipoles $63_1$ to $63_n$ at an inner bottom thereof and disposed so as to be able to come into contact with liquid stored.

The support section moving mechanism 5 includes: a processing head moving mechanism 52 for making it possible to relatively move the processing head 7 with respect to the container group 3 in the Y-axis direction; and a Z-axis moving mechanism 53 as a part of the support section moving mechanism 5 for making it possible to move the electrode array element support sections $4_1$ to $4_n$ which sequentially selectively can support either the electrode array elements $2_1$ to $2_n$ or the dispensing elements $8_1$ to $8_n$ or can support both thereof overlappingly with respect to the processing head 7 in the Z-axis direction.

The CPU+program+memory 9 includes: a reaction control section 91 for instructing the suction and discharge mechanism 83, the processing head moving mechanism 52, the Z-axis moving mechanism 53, a temperature control section, and the like to perform suction and discharge of the liquid stored in a predetermined liquid storing section group $3b$ by the dispensing elements $8_1$ to $8_n$, attachment of the dispensing elements $8_1$ to $8_n$ to the electrode array element support sections $4_1$ to $4_n$, support of the dispensing elements $8_1$ to $8_n$ by the electrode array element support sections $4_1$ to $4_n$, temperature control, and the like; a measurement control section 92 for instructing the applying units $62_1$ to $62_4$, the measurement section 64, the Z-axis moving mechanism 53, and the processing head moving mechanism 52 to perform measurement; and an analysis unit 93 for converting analog data measured by the measurement section into digital data and analyzing the data.

The electrode array element support sections $4_1$ to $4_n$ can support the electrode array elements $2_1$ to $2_n$ and the dispensing elements $8_1$ to $8_n$, respectively, and are electrically connected to the electrodes disposed in the electrode array elements $2_1$ to $2_n$, respectively. As described below, in a case where the dispensing elements $8_1$ to $8_n$ are dispensing tips, each of the electrode array element support sections $4_1$ to $4_n$ includes at least a nozzle and a plug as the suction and discharge mechanism 83. In a case where the dispensing elements $8_1$ to $8_n$ are deformable dispensing tips, each of the electrode array element support sections $4_1$ to $4_n$ includes a support for supporting the deformable dispensing tip in place of the nozzle. In this case, the suction and discharge mechanism 83 includes a movable member for deforming the deformable dispensing tip.

Subsequently, a device for electrical measurement of a target chemical substance 100 according to First Example of the embodiment of the present invention will be described with reference to FIGS. 2 to 7.

The device for electrical measurement of a target chemical substance 100 is incorporated in a housing 11. As illustrated in the figures, the housing 11 includes a main body 12 in which a processing head 71 and a container group 31 as main parts of the device 100 are incorporated, and a lid 13 disposed so as to be able to open and close on an upper side. A reference numeral 14 denotes a touch panel type tablet connected to a main body as an operation panel wirelessly. Reference numerals $21_3$ and $21_4$ denote electrode array elements attached to the processing head 71.

Figure 2:
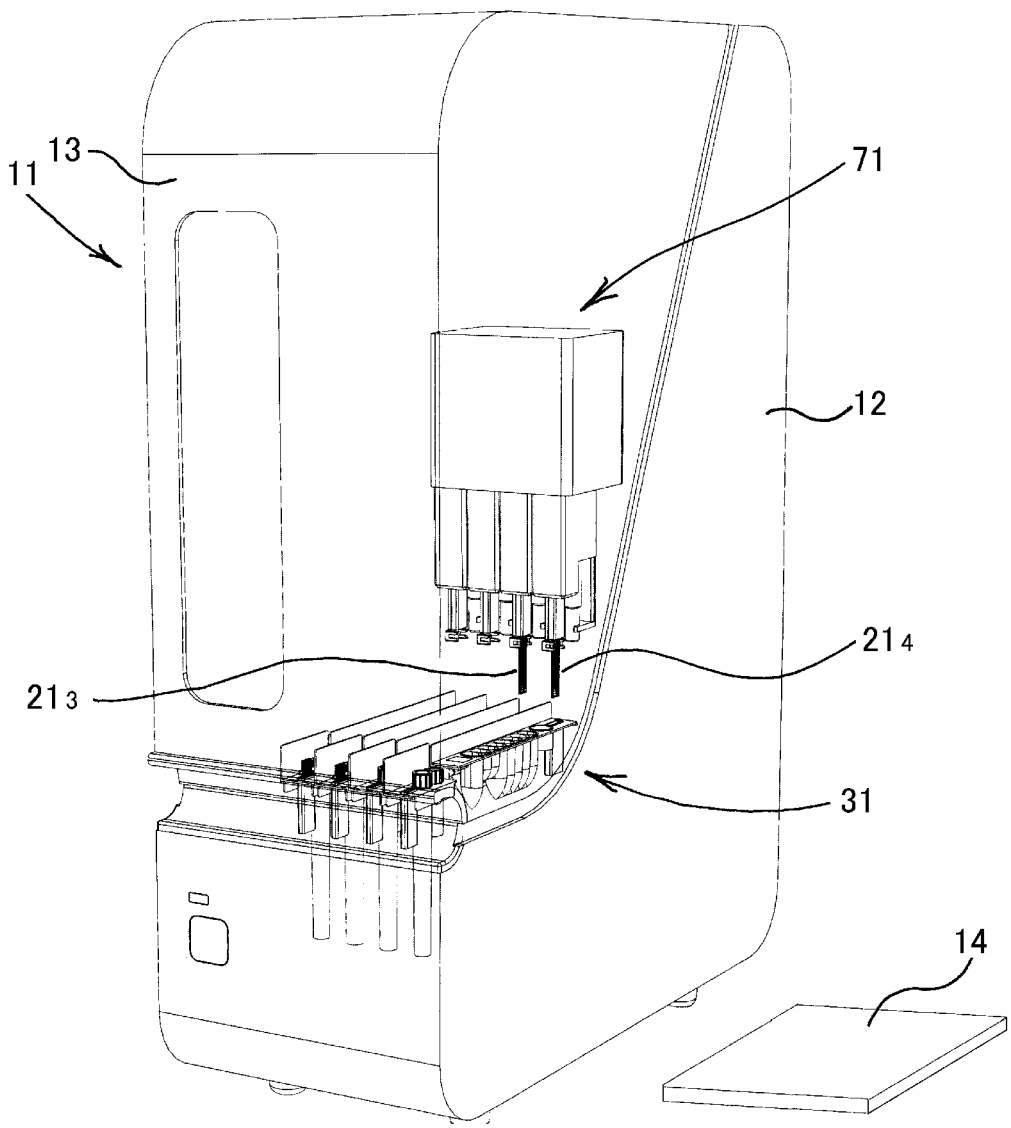
FIG. 2 is a perspective view illustrating an external appearance of a device illustrating First Example obtained by further embodying the device for electrical measurement of a target chemical substance according to the embodiment of the present invention illustrated in FIG. 1.
Figure 3:
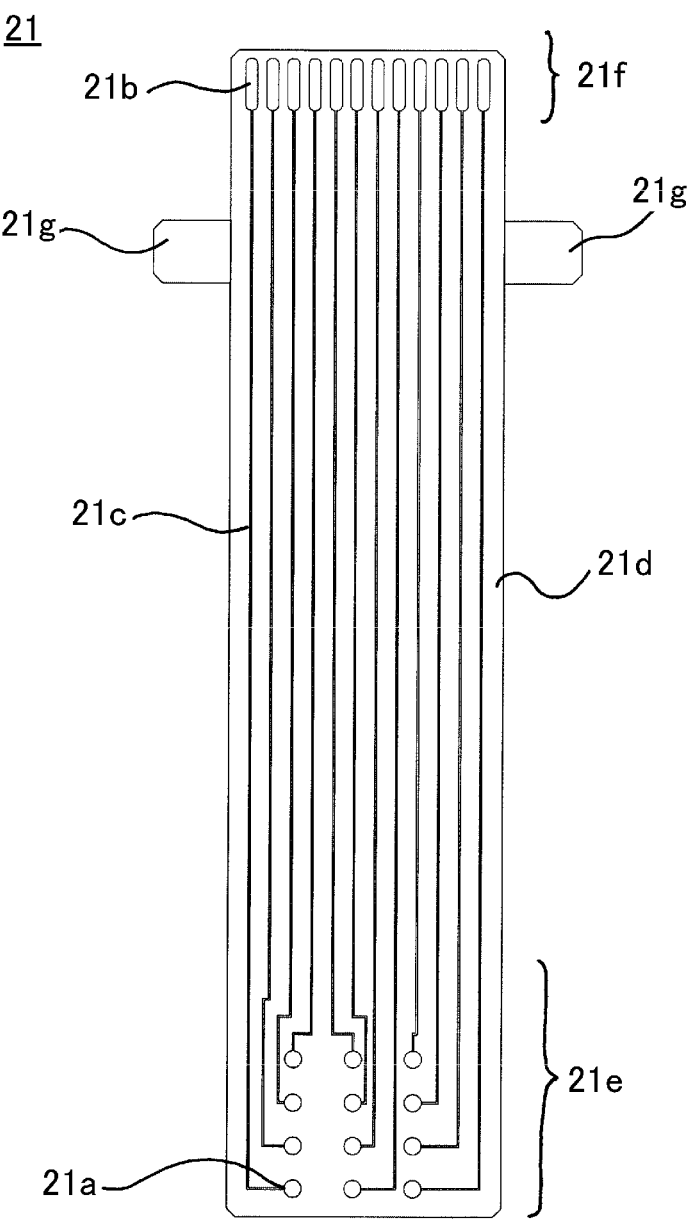
FIG. 3 is an enlarged plan view illustrating an electrode array element illustrated in the device for electrical measurement of a target chemical substance according First Example illustrated in FIG. 2.

FIG. 3 is an enlarged view of the electrode array element $21_4$ of the device for electrical measurement of a target chemical substance 100 illustrated in FIG. 2.

The electrode array element $21_4$ includes: a thin plate-shaped base $21d$ formed of an insulator such as glass, ceramic, or resin; one or more (12 in this example) electrodes $21a$ which are disposed on the base $21d$ and to each of which a test substance having a bonding property to a target chemical substance in a solution stored in the liquid storing section group $31b$ or a measurement container $31c$ is fixed; an electrode array section $21e$ in which the electrodes $21a$ are arrayed and which is disposed on a lower side of the base $21d$; one or more (12 in this example) terminals $21b$ disposed on the base $21d$ so as to correspond to the electrodes $21a$ and electrically connected to the electrodes $21a$ by a conductive wire $21c$; a terminal array section $21f$ in which the terminals $21b$ are arrayed and which is disposed on an upper side of the base $21d$; and two protruding portions $21g$ horizontally protruding from both sides of the base $21d$ on an upper side of the base $21d$, lower than the terminal array section $21f$. The conductive wire $21c$ is embedded in a base or a layered portion covered with or formed of an insulator.

The base $21d$ is formed into a thin rectangular parallelepiped shape having a predetermined height, for example, 1 cm to 10 cm, a predetermined width, for example, 1 cm to 10 cm, and a predetermined thickness shorter than the predetermined height and the predetermined width, for example, 5 mm or less. That is, the predetermined thickness is shorter than the predetermined height and the predetermined width.

Figure 4:
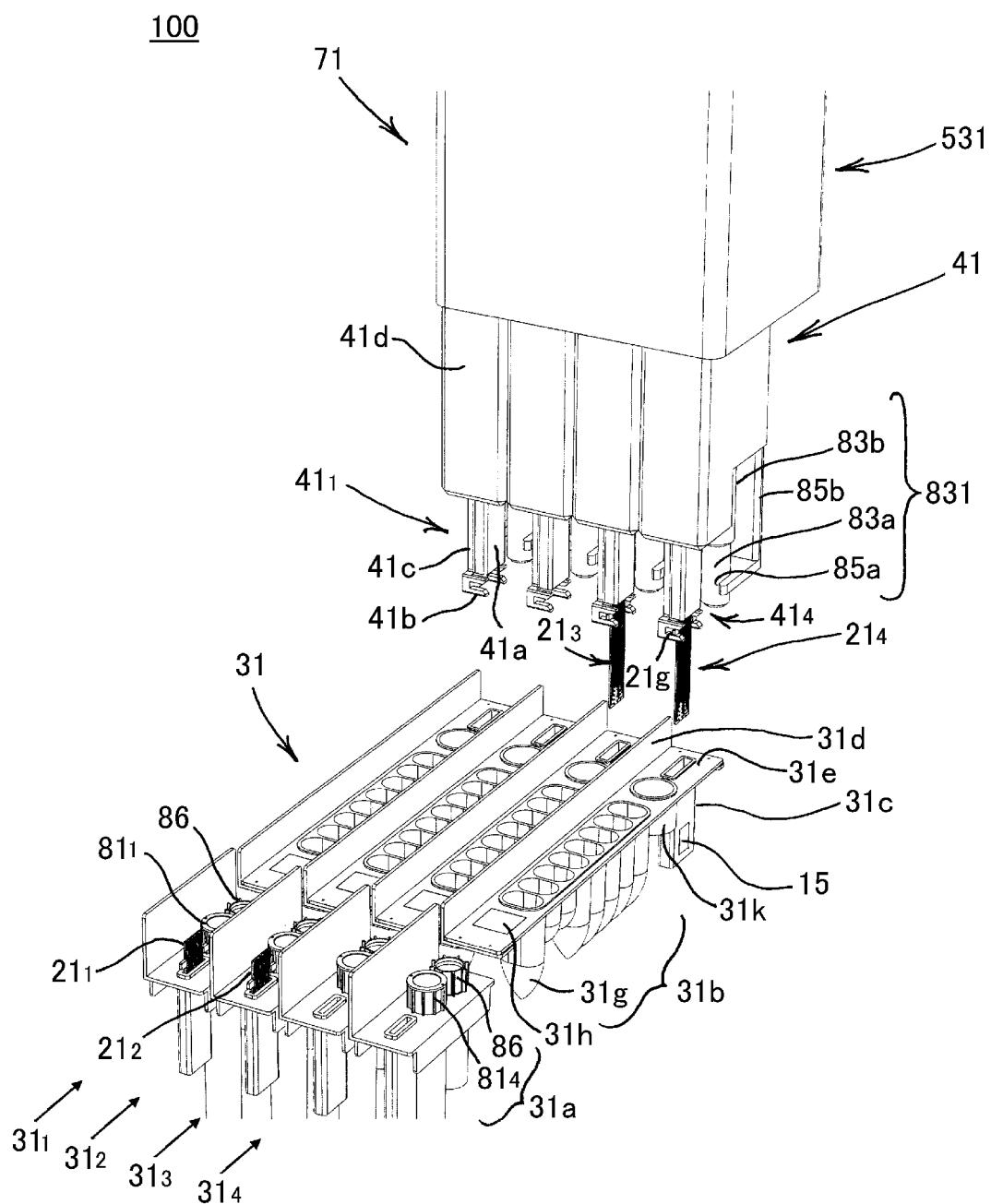
FIG. 4 is a perspective view illustrating a main part of the device for electrical measurement of a target chemical substance according First Example illustrated in FIG. 2.

FIG. 4 more specifically illustrates the main part of the device for electrical measurement of a target chemical substance 100 illustrated in FIG. 2, extracted from the housing 11.

The device for electrical measurement of a target chemical substance 100 roughly includes: a container group 31 including cartridge containers $31_1$ to $31_4$ in which a plurality of storing sections arrayed in a row so as to extend in the Y-axis direction is arrayed in a plurality of rows (four rows in this example) in the X-axis direction; a processing head 71 disposed so as to be relatively movable in a horizontal direction with respect to the container group 31, for example, in the Y-axis direction, and including electrode array element support sections $41_1$ to $41_4$ which can sequentially selectively support a plurality of (four in this example) electrode array elements $21_1$ to $21_4$ and dispensing tips $81_1$ to $81_4$; and the processing head moving mechanism 52 and a Z-axis moving mechanism 531 capable of moving the electrode array element support sections $4_1$ to $4_n$ in the Z-axis direction as the support section moving mechanism 5 for relatively moving the electrode array element support sections $41_1$ to $41_4$ which can selectively support the electrode array elements $21_1$ to $21_4$ or the dispensing tips $81_1$ to $81_4$ disposed in the processing head 71 with respect to the container group 31 in the Y-axis direction.

Figure 5:
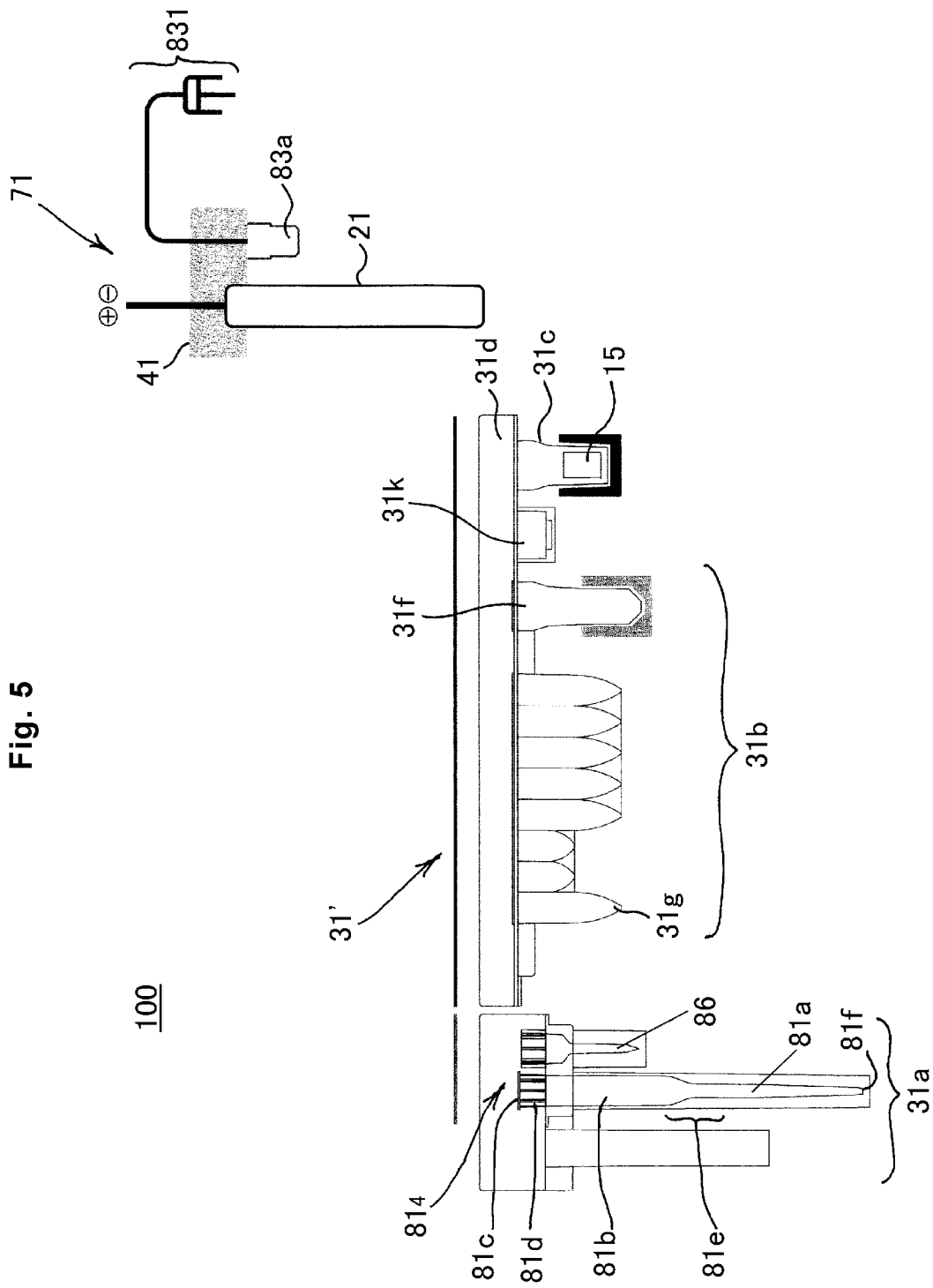
FIG. 5 is a perspective view illustrating another example of the device for electrical measurement of a target chemical substance according to First Example illustrated in FIG. 2.

As illustrated in conjunction with FIG. 5, the cartridge containers $31_1$ to $31_4$ of the container group 31 (31') are formed in a plurality of rows (four rows in this example), and each of the cartridge containers $31_1$ to $31_4$ includes: a tip and the like storing section group $31a$; a liquid storing section group $31b$; a sealing lid storing section $31k$; a measurement container $31c$; a substrate $31e$ having a rectangular flat surface from which these storing section groups protrude downward; and a partition wall $31d$ disposed so as to extend upward along one edge extending in a longitudinal direction of the substrate $31e$ for preventing entry of splashes from an adjacent cartridge container. The liquid storing section group $31b$ includes a sample storing section $31g$ and a reaction container $31f$ (a difference from FIG. 4). A reference numeral $31h$ denotes a two-dimensional barcode for displaying specimen information and test information on the cartridge containers $31_1$ to $31_4$. Note that, in this example, the tip and the like storing section group $31a$ and the liquid storing section group $31b$ are formed separately.

In the processing head 71, the electrode array element support sections $41_1$ to $41_4$ capable of sequentially selectively supporting the electrode array elements $21_1$ to $21_4$ and the dispensing tips $81_1$ to $81_4$ are arrayed in the X-axis direction at the same pitch as an array pitch of the cartridge containers $31_1$ to $31_4$ in the X-axis direction. The electrode array elements $21_1$ to $21_4$ are supported such that a normal direction of an array surface of the base $21d$ on which the electrode array section $21e$ and the terminal array section $21f$ of each of the electrode array elements $21_1$ to $21_4$ are formed faces the X-axis direction.

Array element support 41 includes: a plurality of (four in this example) nozzles $83a$ attachable to the dispensing tips 811 to 814 and communicating with a suction and discharge mechanism; a plug $41a$ fitted with the terminal array section $21f$ of each of the electrode array elements 211 to 214 so as to be electrically connectable to each terminal $21b$ and having an elongated hole-shaped opening in the Y-axis direction; two gripping sections $41b$ capable of holding the two protruding portions $21g$ protruding in the Y-axis direction from each of the electrode array elements 211 to 214 fitted with the plug $41a$ and disposed with a gap in the Y-axis direction; an arm member $41c$ for supporting the two gripping sections $41b$; and an X-axis movable support section $41d$ for supporting the arm member $41c$ such that the arm member $41c$ can slide by a predetermined distance in the X-axis direction based on an instruction from an outside.

The processing head 71 further includes a suction and discharge mechanism 831 communicating with the nozzle $83a$. The suction and discharge mechanism 831 includes: a cylinder $83b$ having a plunger slidably disposed therein; a detachment mechanism 85 including a cutout portion $85a$ having a larger inner diameter than the nozzle $83a$ and having a smaller inner diameter than an outer diameter of a storage tube above a thick tube of each of the dispensing tips 811 to 814, and a detachment member $85b$ including the cutout portion $85a$; the array element support 41 for supporting a cylinder drive mechanism for reciprocating the cylinder $83b$ and the plunger sliding in the cylinder $83b$; and the Z-axis moving mechanism 531 for making the array element support 41 movable in the Z-axis direction.

When the cylinder drive mechanism pushes down the plunger so as to be in a range beyond a suction and discharge range of the plunger, the cylinder drive mechanism pushes down also an upper end of the detachment member $85b$, and the detachment member $85b$ thereby detaches the dispensing tips $81_1$ to $81_4$ from the nozzles $83a$. As the detachment member for the electrode array elements $21_1$ to $21_4$, the gripping section $41b$ is used. Also for the arm member $41c$ supporting the gripping section $41b$, when the cylinder drive mechanism pushes down the plunger so as to be in a range beyond a suction and discharge range of the plunger, the cylinder drive mechanism pushes down also an upper end of the arm member $41c$, and the electrode array elements $21_1$ to $21_4$ are thereby detached from the plugs $41a$.

The processing head 71 further includes a magnetic force mechanism 87 for applying a magnetic force to an inside of each of the dispensing tips $81_1$ to $81_4$ attached to the nozzle. For example, the magnetic force mechanism 87 includes at least: n (four in this example) permanent magnets 871 arrayed at intervals corresponding to the array of the dispensing tips $81_1$ to $81_4$; a magnet array member 872 for supporting the n permanent magnets 871; and an actuator 873 disposed in the Y-axis direction so as to move the magnet array member 872 forward and backward with respect to the dispensing tips $81_1$ to $81_4$ in the Y-axis direction, having a ball screw having one end pivotally supported by the magnet array member and the other end pivotally supported by a ball screw shaft support plate, and a motor for rotationally driving a nut portion screwed with the ball screw built-in, and supported by the processing head 71 (refer to FIG. 12). The processing head 71 further includes: a temperature raising and lowering body $88a$ for controlling the temperature of a liquid sucked into the dispensing tips $81_1$ to $81_n$; a raising and lowering body advancing and retracting drive mechanism $88b$ for advancing or retracting the temperature raising and lowering body $88a$ so as to make the temperature raising and lowering body $88a$ approach the dispensing tips $81_1$ to $81_n$ and the like; and a temperature controller $88c$ for controlling the temperature rising and falling of the temperature raising and lowering body $88a$.

As illustrated in FIG. 5, the tip and the like storing section group $31a$ is stored in a first storing section such that each of the electrode array elements $21_1$ to $21_4$ can be fitted with the plug $41a$ of the array element support 41, the protruding portion $21g$ can be gripped by the gripping section $41b$, and the terminal array section $21f$ of each of the electrode array elements $21_1$ to $21_4$ is exposed to an upper side of the storing section with an elongated hole-shaped opening in the Y-axis direction. The dispensing tips $81_1$ to $81_4$ are stored in a second storing section with an attachment opening $81c$ facing up such that the dispensing tips $81_1$ to $81_4$ are attachable to the nozzles $83a$ of the electrode array element support sections $41_1$ to $41_4$, respectively. A piercing tip 86 is stored in a third storing section such that the piercing tip 86 is attachable to the nozzle $83a$.

As illustrated in FIG. 5, the dispensing tip 81 includes: a tapered cylindrical thin tube $81a$; a thick tube $81b$ communicating with the thin tube $81a$ through a transition portion $81e$; a mouth portion $81f$ which is disposed at a tip end of the thin tube $81a$, can be inserted into a container, and sucks and discharges liquid; an attachment opening $81c$ disposed above the thick tube $81b$ and attachable to the nozzle $83a$ (refer to FIG. 6) communicating with a suction and discharge mechanism for sucking and discharging gas; a plurality of vertically extending ridges $81d$ disposed along an outer periphery of an outer surface of a storage tube on an upper side of the thick tube $81b$ having the attachment opening $81c$; and the transition portion $81e$ disposed between the thin tube $81a$ and the thick tube $81b$.

The liquid storing section group $31b$ includes a plurality of (nine in this example) liquid storing sections capable of storing liquid. Specifically, the liquid storing section group $31b$ includes a sample storing section $31g$ (first liquid storing section) storing, for example, a food extract solution extracted from food as an extracted sample for a test, and a liquid storing section group storing a plurality of liquid storing sections storing various cleaning buffer solutions.

The measurement container $31c$ has an elongated hole-shaped opening with a longitudinal direction in the Y-axis direction, and includes antipoles $63_1$ to $63_4$ at an inner bottom portion thereof so as to be able to come into contact with liquid stored in the container $31c$. The measurement container $31c$ is formed so as to have an inner width longer than the predetermined width of the base $21d$, for example, 1 cm to 10 cm, for example, an inner width of 1.1 cm to 11 cm, and an inner depth longer than the predetermined thickness but shorter than the predetermined width, for example, an inner depth of 1 mm to 10 mm. As a result, even a liquid having a small volume can come into contact with the electrode.

Figure 6:
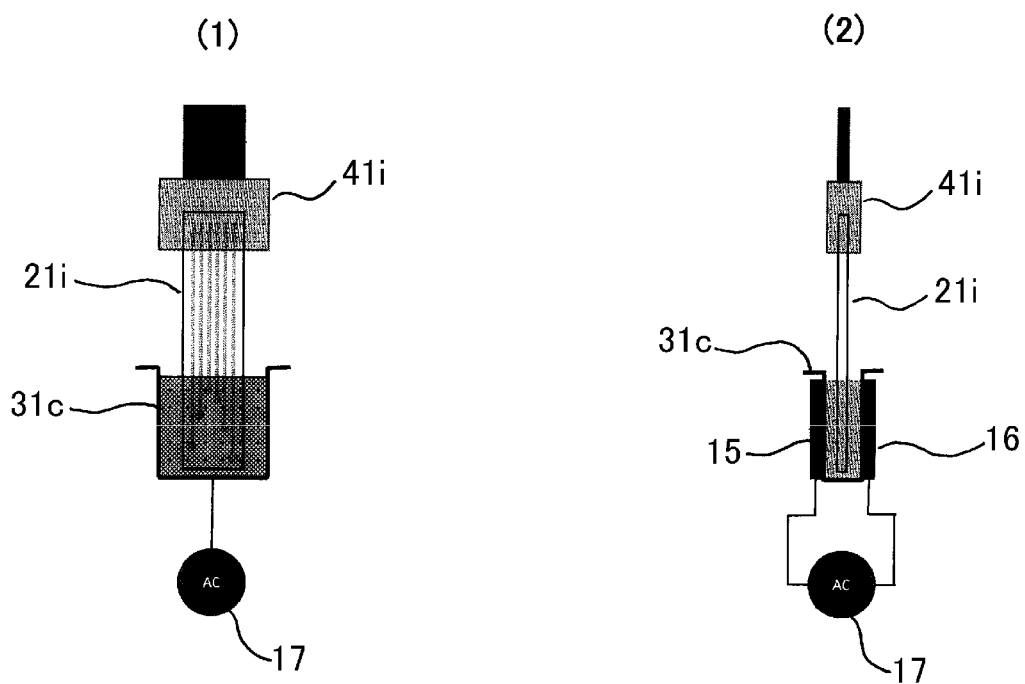
FIG. 6 is an operation explanatory diagram of the device for electrical measurement of a target chemical substance according First Example illustrated in FIG. 3.

As illustrated in FIG. 6, on an outer wall of a side surface having the largest area among side surfaces of the measurement container 31c or in a wall thickness of the outer wall, two non-wetted electrodes 15 and 16 for application of an external electric field for applying Brownian motion to liquid or a solution stored in the measurement container 31c are disposed so as to sandwich the measurement container 31c and not to be in contact with the liquid stored therein. By applying an alternating high voltage between the electrodes, Brownian motion of the solution stored in the measurement container 31c can be activated, encounterability between the electrodes and a target substance in the solution can be enhanced, and a reaction can be accelerated.

Subsequently, an operation in a case where the device for electrical measurement of a target chemical substance 100 and a method therefor according to First Example of the present embodiment are applied to detection of a specific food allergen on the display obligation 7 items (egg, milk, wheat, buckwheat, peanut, shrimp, and a crab) for four kinds of foods will be described with reference to FIG. 5.

Two of the twelve electrodes 21a of the electrode array elements 211 to 214 are electrodes 21a for negative control and positive control. The electrode 21a for negative control is blocked such that an antigen or an antibody is not bonded to the electrode 21a. The electrode 21a for positive control necessarily generates a predetermined electric signal. An antibody (for example, an anti-wheat antibody or an anti-egg antibody) capable of capturing an allergen is fixed to each electrode 21a as a test substance. Furthermore, each liquid storing section of the liquid storing section group 31b includes, in advance, in order, two sets of a liquid storing section storing 100 μL of a food extract solution extracted from food and three liquid storing sections each storing 200 μL of cleaning buffer solution (1×PBS 0.05% Tween). Note that an allergen in each food extract solution is labeled in advance by bonding the allergen to an electrochemically active substance such as a metal complex via an amino group, a carboxyl group, or the like included in the antigen.

In step S1, the processing head moving mechanism 53 moves the processing head 7 in the Y-axis direction so as to located above the first storing section of the tip and the like storing section group 31a storing the electrode array elements $21_1$ to $21_4$. By lowering the plug 41a of each of the electrode array element support sections $41_1$ to $41_4$ disposed on the array element support 41 of the processing head 71 by the Z-axis moving mechanism 531, the terminal array section 21f of each of the electrode array elements $21_1$ to $21_4$ is fitted with and attached to the plug 41a. At this time, the gripping section 41b moves to a position retracted with respect to the plug 41a by the X-axis movable support member 41d. After each of the electrode array elements $21_1$ to $21_4$ is attached to the plug 41a, the X-axis movable support member 41d moves the electrode array elements $21_1$ to $21_4$ in the X-axis direction so as to pass over the plug 41a, and the protruding portions 21g of the electrode array elements $21_1$ to $21_4$ are gripped.

In step S2, the Z-axis moving mechanism 531 raises the electrode array elements $21_1$ to $21_4$ attached to the electrode array element support sections $41_1$ to $41_4$ in the Z-axis direction. Thereafter, the processing head moving mechanism 52 moves the electrode array elements $21_1$ to $21_4$ in the Y-axis direction to locate the electrode array elements $21_1$ to $21_4$ above the sample storing section 31g storing the food extract solution. The Z-axis moving mechanism 531 lowers the electrode array elements $21_1$ to $21_4$, and suction is performed until reaching such a capacity that the electrode array section 21e of each of the electrode array elements $21_1$ to $21_4$ is immersed in the food extract solution to bring the electrode array elements $21_1$ to $21_4$ into contact with the food extract solution.

In step S3, the Z-axis moving mechanism 531 raises the electrode array elements $21_1$ to $21_4$ in the Z-axis direction. Thereafter, the processing head moving mechanism 52 moves the electrode array elements $21_1$ to $21_4$ in the Y-axis direction above the liquid storing section 31b storing a cleaning liquid. The Z-axis moving mechanism 531 lowers the electrode array elements $21_1$ to $21_4$ to bring the electrode array section of each of the electrode array elements $21_1$ to $21_4$ into contact with the cleaning liquid for cleaning. Similarly, cleaning is repeated with respect to other cleaning liquids.

In step S4, the processing head moving mechanism 52 moves the electrode array elements $21_1$ to $21_4$ in the Y-axis direction above the measurement container 31c. The Z-axis moving mechanism 531 lowers the electrode array elements $21_1$ to $21_4$ to bring the electrode array elements $21_1$ to $21_4$ into contact with the solution in the measurement container 31c. While the electrode array section of each of the electrode array elements $21_1$ to $21_4$ is immersed in the solution, the applying units $62_1$ to $62_4$ apply a voltage to an antibody bonding to the electrodes 21a via the counter electrode 63, and the measurement sections $64_1$ to $64_4$ measure the amount of the voltage. The measurement result is digitally converted, is then stored in a storage unit in the CPU+program+memory 9, and is analyzed by the analysis unit 93.

As illustrated in FIG. 6, at least in the measurement step of step S4, by applying the high voltage (1 kV) with an alternating voltage 17 having a predetermined frequency (for example, 20 Hz) through the non-wetted electrodes 15 and 16 for application of an external electric field disposed so as to sandwich the measurement container 31c on an outer surface having the largest area in the measurement container 31c, Brownian motion is applied to an inside of the measurement container 31c to stir the electrolytic solution. A target chemical substance is thereby stirred in a solution to enhance encounterability with a test substance fixed to each of the electrodes of the electrode array elements $21_1$ to $21_4$ and to accelerate a reaction.

Figure 7:
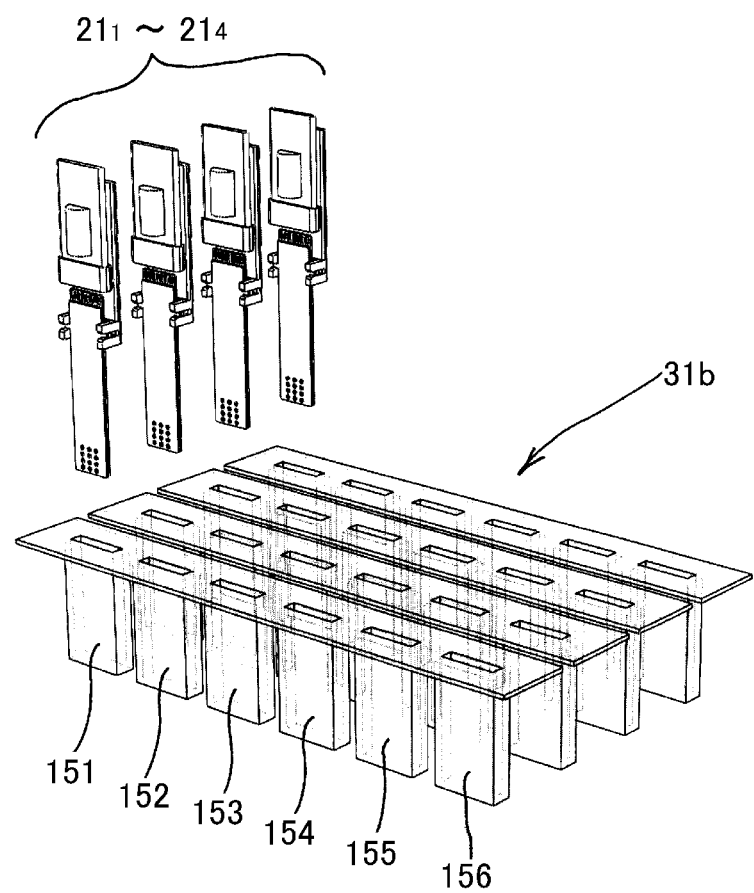
FIG. 7 is a schematic view illustrating another example of a liquid storing section or a measurement container of the device for electrical measurement of a target chemical substance according First Example illustrated in FIG. 2.

FIG. 7 illustrates that each liquid storing section belonging to the liquid storing section group 31b is formed into a rectangular tube shape, and non-wetted electrodes 151 to 156 for application of an external electric field for applying an electric field for stirring to an inside of each liquid storing section are disposed on an outer surface of each rectangular tubular liquid storing section so as to stir the liquid.

Next, a device for electrical measurement of a target chemical substance 101 according to Second Example of the embodiment of the present invention will be described with reference to FIGS. 8 to 11. The basic structure of the device for electrical measurement of a target chemical substance 101 is as illustrated in the block diagram of FIG. 1, but details thereof are as follows.

Figure 8:
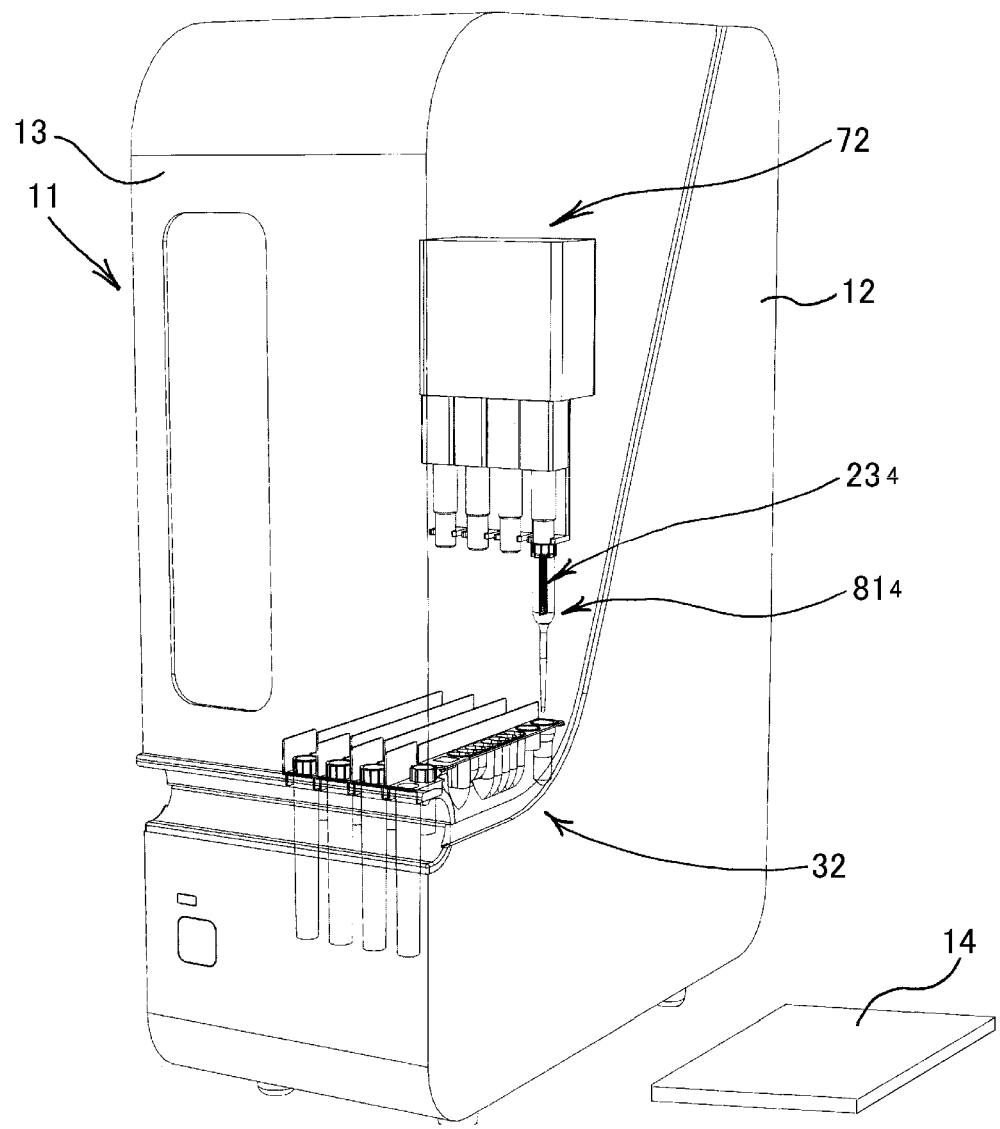
FIG. 8 is a perspective view illustrating an external appearance of a device illustrating Second Example obtained by further embodying the device for electrical measurement of a target chemical substance according to the embodiment of the present invention illustrated in FIG. 1.

FIG. 8 illustrates an external appearance of the device for electrical measurement of a target chemical substance 101.

The device for electrical measurement of a target chemical substance 101 is incorporated in a housing 11 in a similar manner to the above device for electrical measurement of a target chemical substance 100 according to First Example. The housing 11 includes a main body 12 in which a processing head 72 and a container group 32 as main parts of the device 101 are incorporated, and a lid 13 disposed so as to be able to open and close on an upper side. A reference numeral 14 denotes a touch panel type tablet connected to a main body as an operation panel wirelessly. A reference numeral $81_4$ denotes a dispensing tip including an electrode array element $21_4$.

Figure 9:
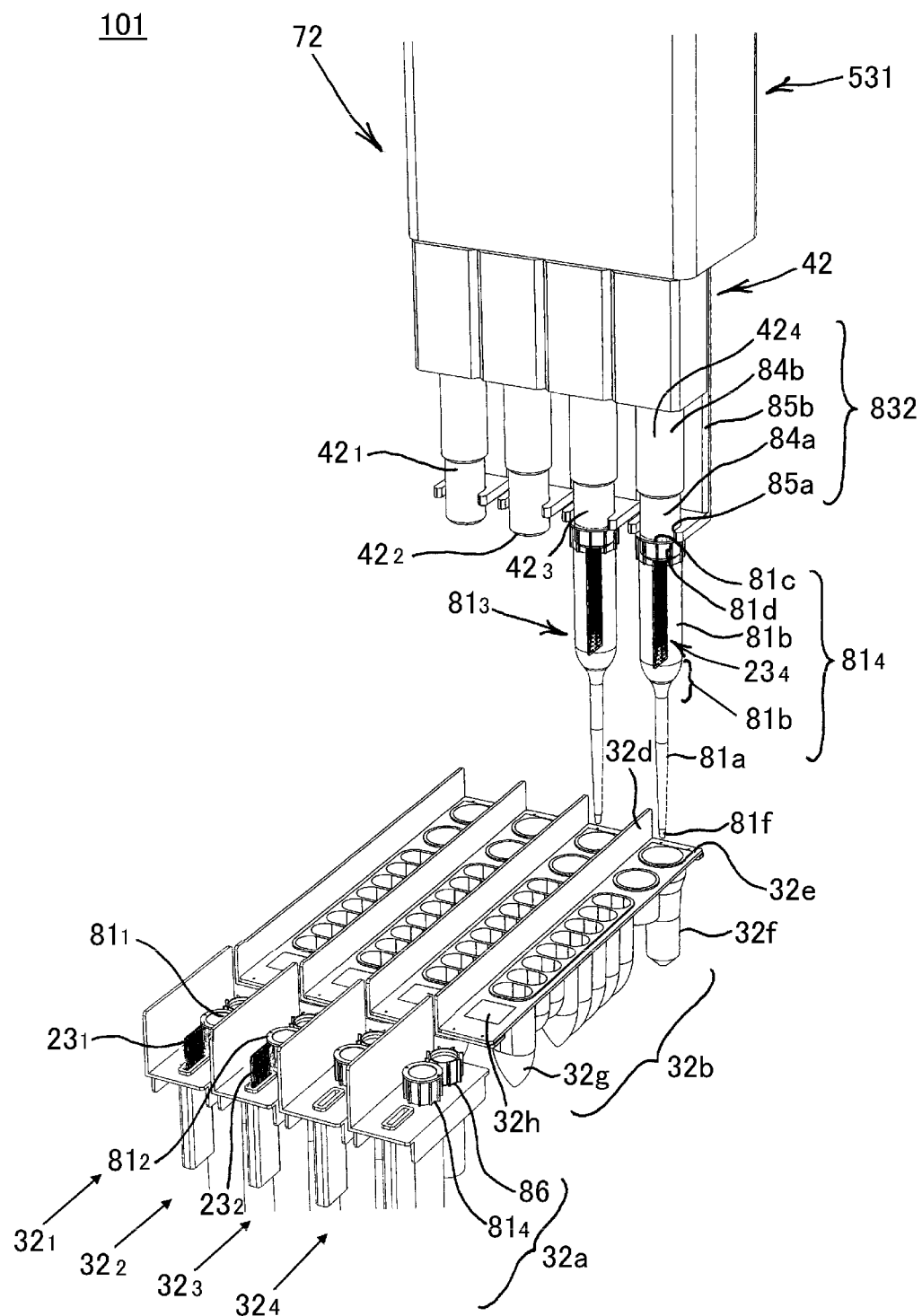
FIG. 9 is a perspective view illustrating a main part of the device for electrical measurement of a target chemical substance according Second Example illustrated in FIG. 8.

FIG. 9 more specifically illustrates the main part of the device for electrical measurement of a target chemical substance 101 illustrated in FIG. 8, extracted from the housing 11.

The device for electrical measurement of a target chemical substance 101 roughly includes: a container group 32 including cartridge containers $32_1$ to $32_4$ in which a plurality of storing sections arrayed in a row so as to extend in the Y-axis direction is arrayed in a plurality of rows (four rows in this example) in the X-axis direction; a processing head 72 disposed so as to be relatively movable in a horizontal direction with respect to the container group 32, for example, in the Y-axis direction, and including electrode array element support sections $42_1$ to $42_4$ which can support a plurality of (four in this example) electrode array elements $23_1$ and $23_4$ and dispensing tips $81_1$ to $81_4$ in this order; and a processing head moving mechanism 52 and a Z-axis moving mechanism 531 capable of moving the electrode array element support sections $42_1$ to $42_4$ in the Z-axis direction as a support section moving mechanism 5 capable of relatively moving the electrode array element support sections $42_1$ to $42_4$ which can overlappingly support the electrode array elements $23_1$ to $23_4$ and the dispensing tips $81_1$ to $81_4$ disposed in the processing head 72 with respect to the container group 32 in the Y-axis direction.

Figure 11:
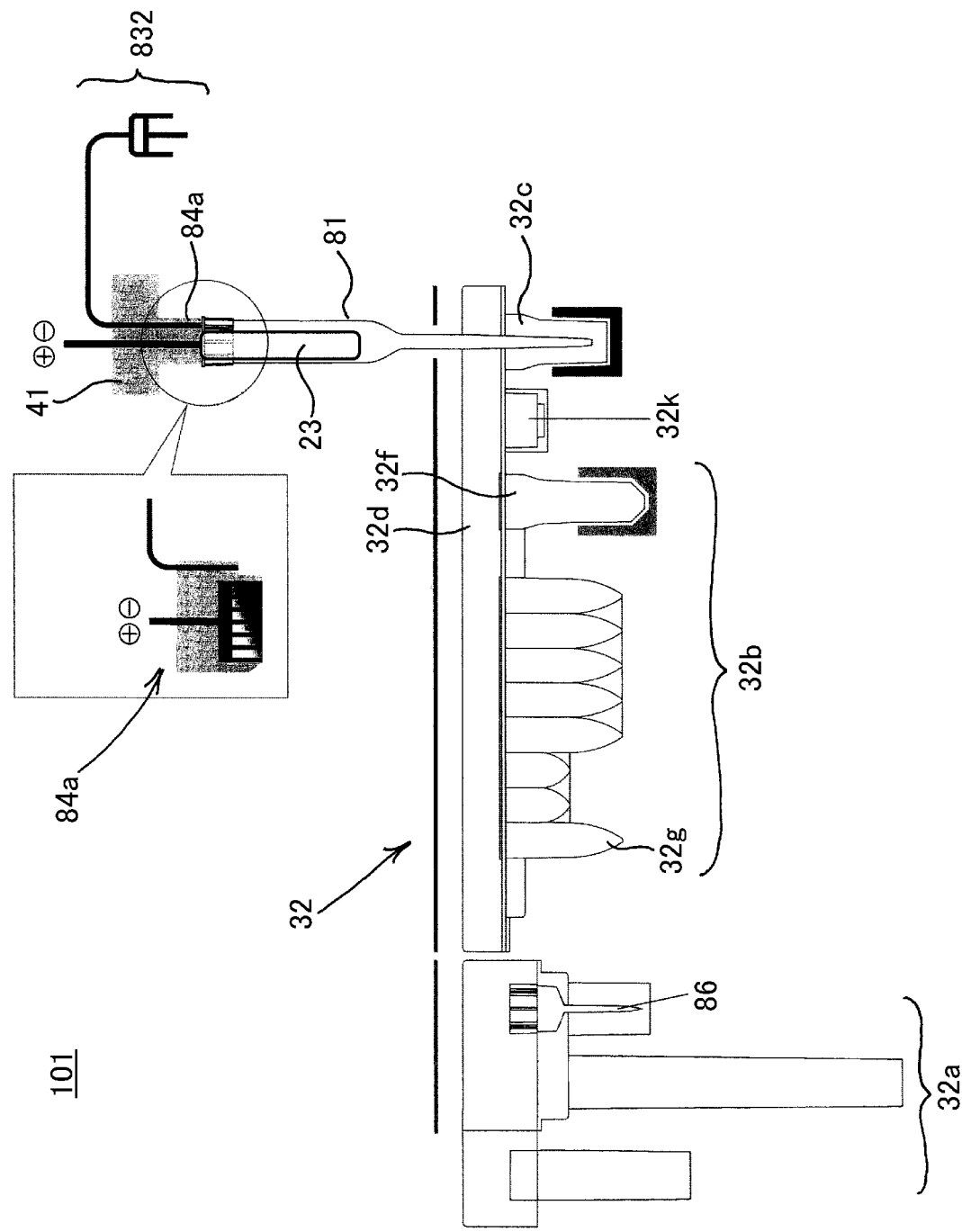
FIG. 11 is an operation explanatory diagram of the device for electrical measurement of a target chemical substance according Second Example illustrated in FIG. 9.

As illustrated in conjunction with FIG. 11, the cartridge containers $32_1$ to $32_4$ of the container group 32 are formed in a plurality of rows (four rows in this example), and each of the cartridge containers $32_1$ to $32_4$ includes: a tip and the like storing section group 32a; a liquid storing section group 32b; a lid storing section 32k for storing a sealing lid used for sealing an opening of a measurement container 32c; the measurement container 32c; a substrate 32e having a rectangular flat surface from which these storing section groups protrude downward; and a partition wall 32d disposed so as to extend upward along one edge extending in a longitudinal direction of the substrate 32e for preventing entry of splashes from an adjacent cartridge container. A reference numeral 32h denotes a two-dimensional barcode for displaying specimen information and test information on the cartridge containers $32_1$ to $32_4$. Note that, in this example, the tip and the like storing section group 32a and the liquid storing section group 32b are formed separately.

In the processing head 72, nozzles 83a as the electrode array element support sections $42_1$ to $42_4$ capable of supporting the dispensing tips $81_1$ to $81_4$ alone or the electrode array elements $23_1$ to $23_4$ and the dispensing tips $81_1$ to $81_4$ while the electrode array elements $23_1$ to $23_4$ and the dispensing tips $81_1$ to $81_4$ are attached in this order and the electrode array elements $23_1$ to $23_4$ are enclosed in thick tubes of the dispensing tips $81_1$ to $81_4$ are arrayed in the X-axis direction at the same pitch as the array pitch of the cartridge containers $32_1$ to $32_4$ in the X-axis direction. Note that the electrode array elements $23_1$ to $23_4$ are disposed such that a normal direction of a plane having the largest area of the base 23d faces the X-axis direction.

Figure 10:
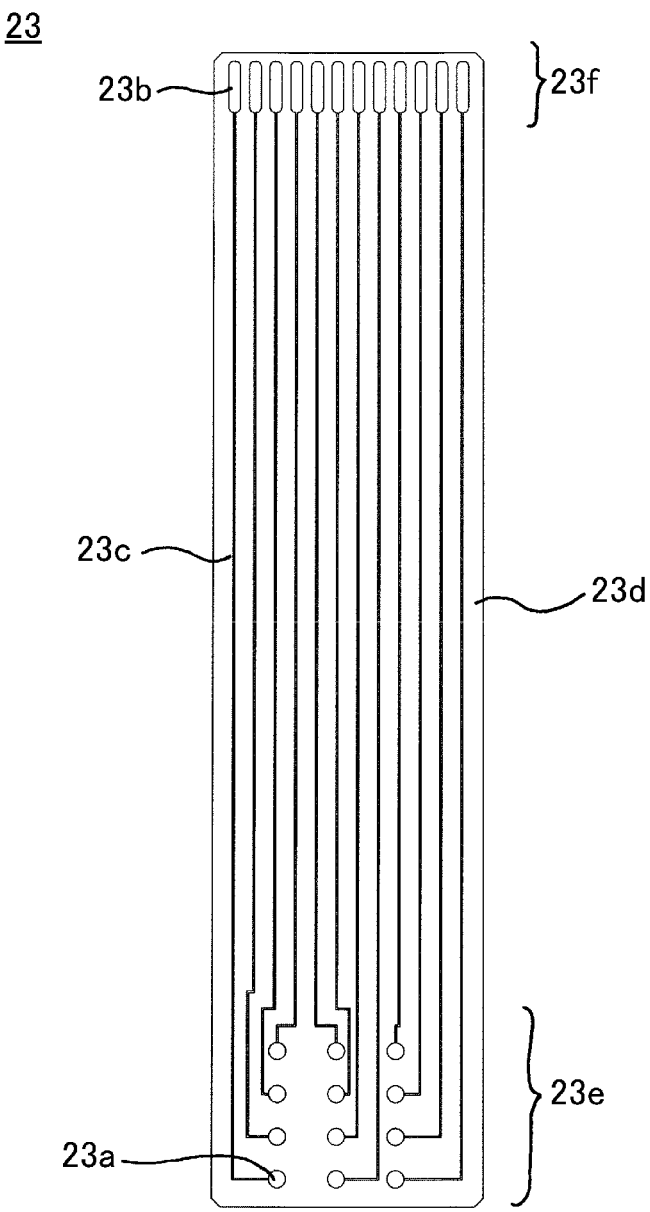
FIG. 10 is an enlarged plan view illustrating an electrode array element illustrated in the device for electrical measurement of a target chemical substance according Second Example illustrated in FIG. 9.

FIG. 10 is an enlarged view of the electrode array element 23 of the device for electrical measurement of a target chemical substance 101 illustrated in FIG. 9.

The electrode array element 23 includes: a thin plate-shaped base 23d formed of an insulator such as glass, ceramic, or resin; one or more (12 in this example) electrodes 23a which are disposed on the base 23d and to each of which a test substance having a bonding property to a target chemical substance in a solution stored in the liquid storing section group 32b or the measurement container 32c is fixed; an electrode array section 23e in which the electrodes 23a are arrayed and which is disposed on a lower side of the base 23d; one or more (12 in this example) terminals 23b disposed on the base 23d so as to correspond to the electrodes 23a and electrically connected to the electrodes 23a by a conductive wire 23c; and a terminal array section 23f in which the terminals 23b are arrayed and which is disposed on an upper side of the base 23d. The conductive wire 23c is embedded in a base or a layered portion covered with or formed of an insulator.

Returning to FIG. 9, the electrode array element support sections $42_1$ to $42_4$ include a plurality of (four in this example) nozzles 84a attachable to the dispensing tips $81_1$ to $81_4$ and the electrode array elements $23_1$ to $23_4$ and communicating with a suction and discharge mechanism. Each of the nozzles 84a includes a plug fitted with the terminal array section 23f of each of the electrode array elements $23_1$ to $23_4$ so as to be electrically connectable to each terminal 23b and having an elongated hole-shaped opening in the Y-axis direction.

The processing head 72 further includes a suction and discharge mechanism 832 communicating with the nozzle 84a. The suction and discharge mechanism 832 includes: a cylinder 84b having a plunger slidably disposed therein; a detachment mechanism 85 including a cutout portion 85a having a larger inner diameter than the nozzle 84a and having a smaller inner diameter than an outer diameter of a storage tube above a thick tube of each of the dispensing tips $81_1$ to $81_4$, and a detachment member 85b including the cutout portion 85a; an array element support 42 for supporting a cylinder drive mechanism for reciprocating the cylinder 84b and the plunger sliding in the cylinder 84b; and the Z-axis moving mechanism 531 for making the array element support 42 movable in the Z-axis direction.

Note that the detachment member 85b, the magnetic force mechanism 44, the temperature raising and lowering body 481, the dispensing tip 81, and the like have already been described above, and therefore explanation thereof is omitted.

As illustrated in FIG. 9, the tip and the like storing section group 32a is stored in a first storing section such that each of the electrode array elements $23_1$ to $23_4$ can be fitted with a plug disposed at a lower end of the nozzle 84a as the electrode array element support section 43, and the terminal array section 23f of each of the electrode array elements $23_1$ to $23_4$ is exposed to an upper side of the storing section with an elongated hole-shaped opening in the Y-axis direction. The dispensing tips $81_1$ to $81_4$ are stored in a second storing section with an attachment opening 81c facing up such that the dispensing tips $81_1$ to $81_4$ are attachable to the nozzles 84a of the electrode array element support section 43. A piercing tip 86 is stored in a third storing section such that the piercing tip 86 is attachable to the nozzle 84a. Note that the dispensing tip 81 has been described above, and therefore description thereof is omitted here.

The liquid storing section group 32b includes a plurality of (nine in this example) liquid storing sections capable of storing liquid. More specifically, as illustrated in conjunction with FIG. 11, for example, the liquid storing section group 32b includes: a sample storing section 32g (first liquid storing section, counting method is the same as in the liquid storing section group 32b) for storing a sample collected from a subject, such as serum, plasma, whole blood, or body fluid in order to specify bacteria or viruses of infectious diseases which the subject has developed; a magnetic particle suspension storing section used for collecting bacteria and the like (second liquid storing section); a storing section for storing 40 µL of a protein denaturating enzyme solution (Lysis 1) for crushing bacteria and cells (third liquid storing section); a storing section for storing 200 µL of a proteolytic enzyme solution (Lysis 2) (fourth liquid storing section); a storing section for storing 500 µL of a separated extraction solution (bonding buffer solution, NaCl, SDS, and isopropanol) (fifth liquid storing section and sixth liquid storing section); a storing section for storing 700 µL of cleaning liquid (water and isopropanol) (seventh liquid storing section); a dissociated solution (eighth liquid storing section); and a temperature-controllable reaction container $32f$ (ninth liquid storing section).

Furthermore, the measurement container $32c$ also serves as a PCR container capable of performing temperature control so as to make amplification of an extracted nucleic acid possible. The liquid storing section group $32b$ further includes a lid storing section $32k$ for storing a sealing lid which is used for sealing the measurement container $32c$ and which can be pierced.

Subsequently, the device for electrical measurement of a target chemical substance 101 according to Second Example of the present embodiment and an operation of a method therefor will be described with reference to FIGS. 11 and 12. Here, whether there is a bacterium to cause a predetermined infectious disease in a specimen of a subject is tested. Steps S11 to S19 correspond to a nucleic acid extraction step.

In step S11, by operating a touch panel or the like of the operation panel 14, an instruction to start test processing of an infectious disease is given.

In step S12, an extraction/reaction control section 91 disposed in the CPU+program+memory 9 (information processing device) of the device for electrical measurement of a target chemical substance 101 instructs the processing head moving mechanism 52 to move the processing head 72 in the Y-axis direction above the piercing tip 86 stored in the tip and the like storing section group $32a$ of each of the cartridge containers 321 to 324. Thereafter, by driving the Z-axis moving mechanism 531, the nozzle $84a$ is lowered, is attached to the piercing tip 86, and is raised. The processing head moving mechanism 52 locates the piercing tip 86 above the second liquid storing section of the liquid storing section group $32b$ of the container group 32. The Z-axis moving mechanism 531 lowers the piercing tip 86, and thereby pierces a film covering an opening of the liquid storing section. Similarly, by moving the processing head 72 in the Y-axis direction, another liquid storing section and the reaction container $32f$ in the liquid storing section $32b$ are also pierced sequentially.

In step S13, the piercing tip 86 is detached into the tip and the like storing section group $32a$ using the detachment mechanism 85. Thereafter, the processing head 72 is moved to the tip and the like storing section group $32a$ storing the dispensing tips $81_1$ to $81_4$ in the Y-axis direction. The Z-axis moving mechanism 531 lowers the nozzles $84a$, and the dispensing tips $81_1$ to $81_4$ are thereby attached to the processing head 72 via the nozzles $84a$. Subsequently, the Z-axis moving mechanism 531 raises the dispensing tips $81_1$ to $81_4$, and then the processing head moving mechanism 52 moves the dispensing tips $81_1$ to $81_4$ in the Y-axis to the sample storing section $32g$ (first liquid storing section) storing a parent specimen. Thereafter, the Z-axis moving mechanism 531 lowers mouth portions $81f$ of the dispensing tips $81_1$ to $81_4$ for insertion. The suction and discharge mechanism 832 raises and lowers a plunger. The sample liquid stored in the sample storing section $32g$ is thereby repeatedly sucked and discharged such that the sample is suspended in the liquid. Thereafter, the sample liquid is sucked into the dispensing tips $81_1$ to $81_4$. The processing head 72 moves the sample liquid in the Y-axis direction while the sample liquid is sucked into the dispensing tips $81_1$ to $81_4$, and moves the sample liquid to a third liquid storing section storing Lysis 1 (enzyme) as a separated extraction solution. The thin tube $81a$ of each of the dispensing tips $81_1$ to $81_4$ is inserted into the third liquid storing section through a hole of a pierced film. Suction and discharge for stirring the sample liquid and the Lysis 1 are repeated.

In step S14, the whole amount of the stirred liquid is sucked by the dispensing tips 811 to 814, is stored in the reaction container $32f$ (ninth liquid storing section) formed of a reaction tube held in a storing hole set at 55° C. by constant temperature controller, and is incubated. A protein contained in the sample is thereby denatured. After a lapse of predetermined time, the processing head moving mechanism 52 moves the dispensing tips 811 to 814 which have sucked the reaction liquid to a fourth liquid storing section of each of the cartridge containers 321 to 324. The Z-axis moving mechanism 531 and the suction and discharge mechanism 832 mix the reaction liquid with the whole amount of Lysis 2 stored in the fourth liquid storing section to lower the molecular weight of the protein.

In step S15, a bonding buffer solution as a separated extraction solution stored in the fifth liquid storing section and the reaction solution are stirred to further dehydrate a solubilized protein, and a nucleic acid or a fragment thereof is dispersed in the solution.

In step S16, using the dispensing tips $81_1$ to $81_4$, the thin tube is inserted into the fourth liquid storing section through the hole of the film, and the whole amount is sucked. The Z-axis moving mechanism 531 raises the dispensing tips $81_1$ to $81_4$, and transfers the reaction solution to the second liquid storing section. By repeating suction and discharge of a magnetic particle suspension liquid and the reaction solution stored in the second liquid storing section using the suction and discharge mechanism 832, mixing and stirring are performed. A cation structure in which a Na+ ion is bonded to a hydroxy group formed on a surface of silica or the like covering each magnetic particle contained in the magnetic particle suspension is formed. Therefore, negatively charged DNA is captured by magnetic particles.

Figure 12:
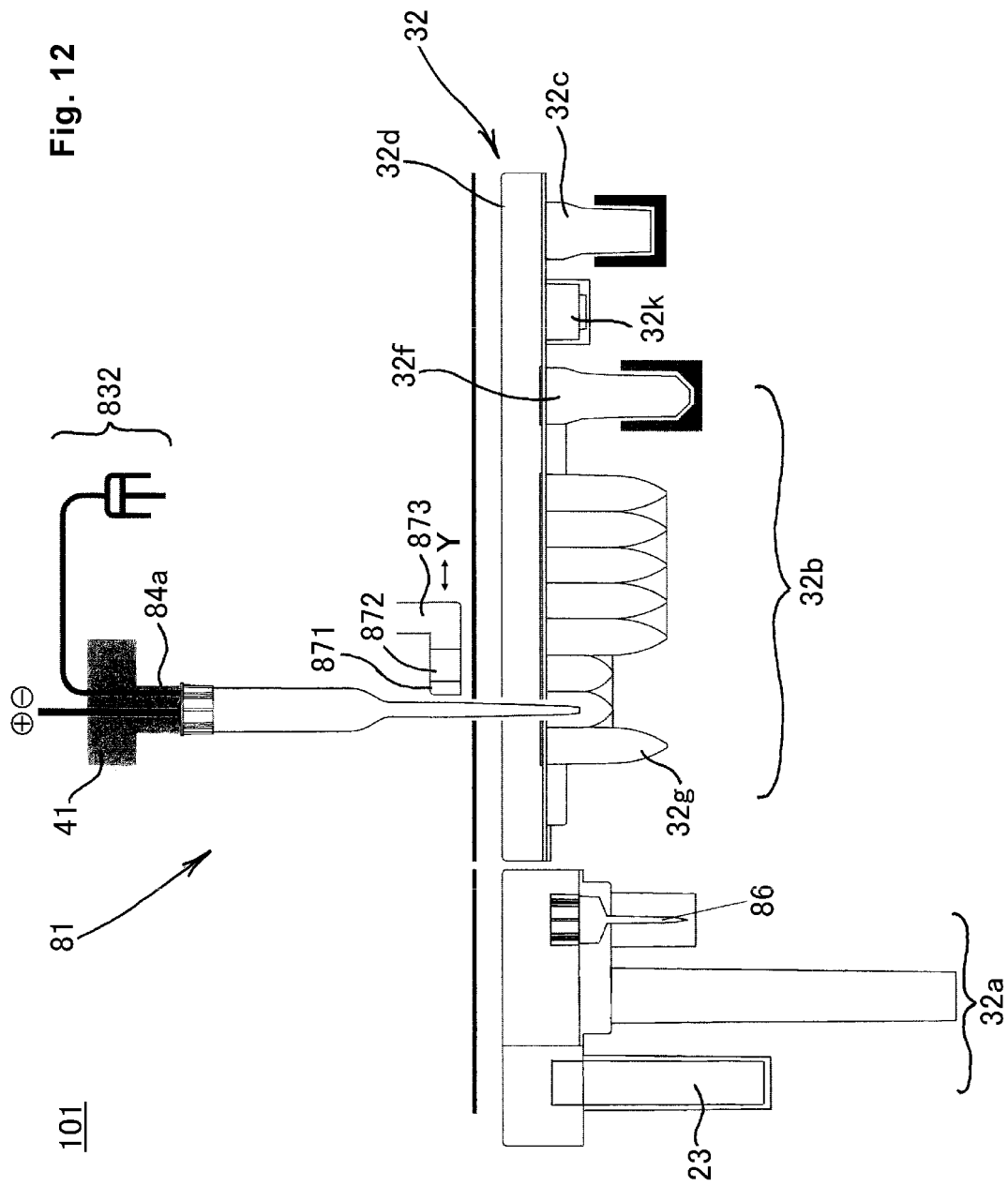
FIG. 12 is an operation explanatory diagram of the device for electrical measurement of a target chemical substance according Second Example illustrated in FIG. 9.

In step S17, as illustrated in FIG. 12, by making the magnet 871 of the magnetic force mechanism 87 approach the thin tube $81a$ of each of the dispensing tips $81_1$ to $81_4$, the magnetic particles are adsorbed by an inner wall of the thin tube $81a$ of each of the dispensing tips $81_1$ to $81_4$. The Z-axis moving mechanism 531 raises the magnetic particles while the magnetic particles are adsorbed by the thin tubes $81a$ of each of the dispensing tips $81_1$ to $81_4$. The processing head moving mechanism 52 moves the dispensing tips $81_1$ to $81_4$ from the second liquid storing section to the sixth liquid storing section, and the thin tube is inserted into the sixth liquid storing section through the hole of the pieced film.

While a magnetic force to an inside of the thin tube $81a$ of each of the dispensing tips $81_1$ to $81_4$ is removed by separating the magnet 871 of the magnetic force mechanism 87 from the thin tube, a cleaning liquid 1 (NaCl, SDS, and isopropanol) stored in the sixth liquid storing section is repeatedly sucked and discharged. The magnetic particles are thereby detached from the inner wall, are stirred in the cleaning liquid 1, and cleaning is thereby performed. Thereafter, while the magnetic particles are adsorbed by the inner wall of the thin tube 81a of each of the dispensing tips $81_1$ to $81_4$ by making the magnet of the magnetic force mechanism 87 approach the thin tube again, the Z-axis moving mechanism 531 raises the dispensing tips $81_1$ to $81_4$, and then the processing head moving mechanism 52 moves the dispensing tips $81_1$ to $81_4$ from the sixth liquid storing section to the seventh liquid storing section.

In step S18, the thin tube of each of the dispensing tips $81_1$ to $81_4$ is inserted through the hole of the film using the Z-axis moving mechanism 531. While a magnetic force to an inside of the thin tube of each of the dispensing tips $81_1$ to $81_4$ is removed by separating the magnet of the magnetic force mechanism 87 from the thin tube, a cleaning liquid 2 (isoproanol) stored in the seventh liquid storing section is repeatedly sucked and discharged. The magnetic particles are thereby stirred in the liquid, NaCl and SDS are removed, and cleaning is performed. Thereafter, while the magnetic particles are adsorbed by the inner wall of the thin tube of each of the dispensing tips $81_1$ to $81_4$ by making the magnet of the magnetic force mechanism 87 approach the thin tube again, the Z-axis moving mechanism 531 raises the dispensing tips $81_1$ to $81_4$, and then the processing head moving mechanism 52 moves the dispensing tips $81_1$ to $81_4$ from the seventh liquid storing section to the eighth liquid storing section storing distilled water.

In step S19, the Z-axis moving mechanism 531 lowers the thin tube of each of the dispensing tips $81_1$ to $81_4$ through the hole. By repeating suction and discharge of the distilled water at a slow flow rate while the magnetic force is applied to an inside of the thin tube 81a of each of the dispensing tips $81_1$ to $81_4$, the cleaning liquid 2 (isopropanol) is replaced with the distilled water, and is removed. Thereafter, by sucking and discharging the magnetic particles repeatedly into distilled water as the dissociated solution stored in the eighth liquid storing section while the magnet of the magnetic force mechanism 87 is separated from the thin tube of each of the dispensing tips $81_1$ to $81_4$ and the magnetic force is removed, stirring is performed, and a nucleic acid retained by the magnetic particles or a fragment thereof is dissociated (eluted) from the magnetic particles into the liquid. Thereafter, by making the magnet 871 approach the thin tube 81a of each of the dispensing tips $81_1$ to $81_4$, a magnetic field is applied to an inside of the thin tube and the magnetic particles are adsorbed by the inner wall, and the liquid is left such that the extracted nucleic acid or the like is contained in the eighth liquid storing section. The processing head moving mechanism 52 moves the dispensing tips $81_1$ to $81_4$ to the eighth liquid storing section holding the cleaning liquid 3. By repeating suction and discharge with the magnetic field removed, the magnetic particles are discharged together with the cleaning liquid 3 while the magnetic particles are resuspended to clean the dispensing tips $81_1$ to $81_4$.

Hereinafter, steps S20 to S25 correspond to a nucleic acid amplification and measurement step.

In step S20, the processing head moving mechanism 52 moves the processing head 72. A solution containing a nucleic acid or the like stored in the eighth liquid storing section is sucked, is transferred to the PCR container 32c storing an amplification solution in advance, is discharged, and is introduced into the container. The PCR container 32c contains a primer for amplifying a characteristic base sequence portion of a target bacterium or a target virus of an infectious disease to be detected in advance. If the target bacterium or the like exists, the base sequence portion is amplified. The processing head moving mechanism 52 returns the dispensing tips $81_1$ to $81_4$ to tip and the like storing section 32a. The dispensing tips $81_1$ to $81_4$ are detached by the detachment member 85b. The nozzle 84a is moved again above the sealing lid storing section 32k. By lowering the nozzle 84a using the Z-axis moving mechanism 531, a recess on an upper side of the sealing lid is fitted with a lower end of the nozzle 84a for attachment. The Z-axis moving mechanism 531 lowers the sealing lid, and the sealing lid is fitted with and attached to an opening of the PCR container-measurement container 32c, and is sealed.

In step S21, when amplification of a nucleic acid extracted by performing temperature control based on a PCR method is completed, the sealing lid is pierced by the piercing tip 86, and the measurement control section 92 instructs the processing head moving mechanism 52 to bring the processing head 72 above the storing section of the piercing tip 86 of the tip and the like storing section group 32a. The piercing tip 86 is detached by the detachment member. Furthermore, the processing head 72 is moved in the Y-axis direction above the storing sections of the electrode array elements $23_1$ to $23_4$. The Z-axis moving mechanism 531 lowers the nozzles 84a, and the electrode array elements $23_1$ to $23_4$ are attached to the plugs disposed at lower ends of the nozzles 84a. Subsequently, the Z-axis moving mechanism 531 raises the nozzles 84a. Thereafter, the processing head 72 is moved in the Y-axis direction above the storing sections of the dispensing tips $81_1$ to $81_4$, and is lowered such that the dispensing tips $81_1$ to $81_4$ are attached to the nozzles 84a while the electrode array elements $23_1$ to $23_4$ are attached to the nozzles 84a to form a combination state in which the electrode array elements $23_1$ to $23_4$ are supported inside the dispensing tips $81_1$ to $81_4$.

In step S21, in that state, using the dispensing tips $81_1$ to $81_4$, a liquid storing section storing a solution of an electrochemically active substance such as an intercalating agent or a metal complex is prepared in the liquid storing section group or the like. The intercalating agent or the like is sucked from the liquid storing section. The processing head moving mechanism 52 is instructed to move the processing head 72 in the Y axis direction above the measurement container 32c. By lowering the dispensing tips $81_1$ to $81_4$ and the electrode array elements $23_1$ to $23_4$ by the Z-axis moving mechanism 531, the intercalating agent or the like is discharged, mixing with an amplified product is performed, and suction and discharge are repeated. A double stranded base sequence generated by hybridization between the test substance fixed to each electrode 23a of the electrode array elements $23_1$ to $23_4$ and a target chemical substance is labeled with the intercalating agent or the like. A change in an electric signal is measured by applying a predetermined voltage by the applying unit. Presence or absence and the amount of bonding between the amplified product and the test carrier fixed to each electrode are measured.

Subsequently, a device for electrical measurement of a target chemical substance 102 according to Third Example of the embodiment of the present invention will be described with reference to FIG. 13. The basic structure of the device for electrical measurement of a target chemical substance 102 is as illustrated in the block diagram of FIG. 1, but details thereof are as follows.

The device for electrical measurement of a target chemical substance 102 roughly includes: a container group 33 including cartridge containers $33_1$ to $33_4$ in which a plurality of storing sections arrayed in a row so as to extend in the Y-axis direction is arrayed in a plurality of rows (four rows in this example) in the X-axis direction; a processing head 73 (refer to FIG. 14) disposed so as to be relatively movable in a horizontal direction with respect to the container group 33, for example, in the Y-axis direction, and including electrode array element support sections $43_1$ to $43_4$ which can support a plurality of (four in this example) electrode array elements $22_1$ to $22_4$ described below; and a processing head moving mechanism 52 and a Z-axis moving mechanism 531 capable of moving the electrode array elements $22_1$ to $22_4$ or the dispensing tips $81_1$ to $81_4$ in the Z-axis direction as a support section moving mechanism 5 capable of relatively moving the electrode array element support sections $43_1$ to $43_4$ disposed in the processing head 73, that is, the electrode array elements $22_1$ to $22_4$ supported by the electrode array element support sections $43_1$ to $43_4$ with respect to the container group 33 in the Y-axis direction.

Figure 13:
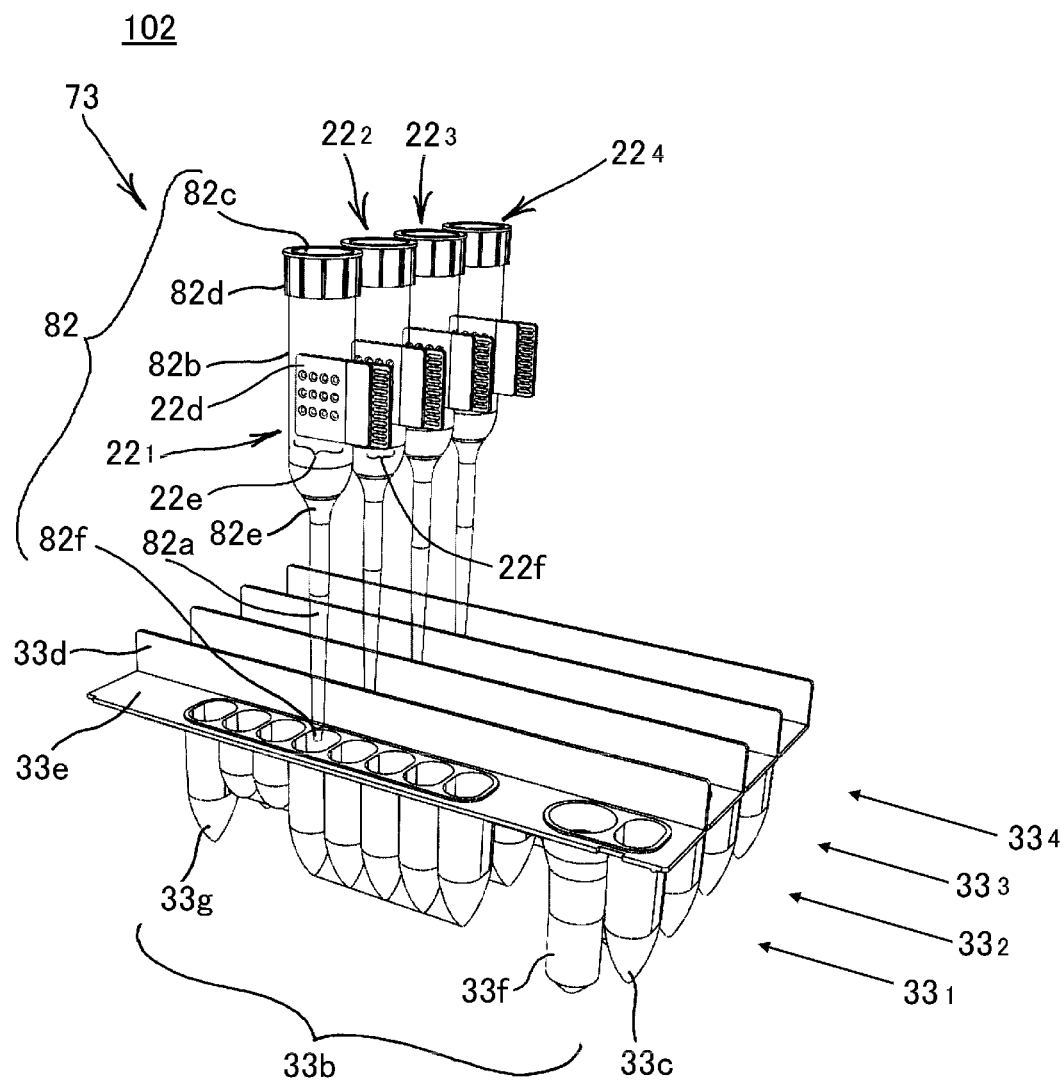
FIG. 13 is a perspective view illustrating a device for electrical measurement of a target chemical substance according to Third Example of the present invention.

As illustrated in FIG. 13, the cartridge containers $33_1$ to $33_4$ of the container group 33 are formed in a plurality of rows (four rows in this example), and each of the cartridge containers $33_1$ to $33_4$ includes: a tip and the like storing section group (not illustrated); a liquid storing section group 33b; a measurement container 33c; a substrate 33e having a rectangular flat surface from which these storing section groups protrude downward; and a partition wall 33d disposed so as to extend upward in a longitudinal direction of the substrate 33e for preventing entry of splashes from an adjacent cartridge container. Note that, in this example, the tip and the like storing section group 33a and the liquid storing section group 33b are formed separately. In FIG. 13, a reference numeral 33g denotes a sample storing section, and a reference numeral 33f denotes a reaction container.

In the processing head 73, as the electrode array element support sections $43_1$ to $43_4$ capable of being attached to and supporting the electrode array elements $22_1$ to $22_4$, nozzles 83a (refer to FIG. 4) communicating with a suction and discharge mechanism 83 for sucking and discharging gas and plugs 43a are arrayed in the X-axis direction at the same pitch as an array pitch of the cartridge containers $33_1$ to $33_4$ in the X-axis direction.

As illustrated in FIG. 13, each of the electrode array elements $22_1$ to $22_4$ includes, as a base, a dispensing tip 82 as a dispensing element and a plate 22d. The dispensing tip 82 includes: a tapered cylindrical thin tube 82a; a thick tube 82b communicating with the thin tube 82a through a transition portion 82e; a mouth portion 82f which is disposed at a tip end of the thin tube 82a, can be inserted into a container, and sucks and discharges liquid; an attachment opening 82c disposed in a storage tube above the thick tube 82b and attachable to the nozzle; a plurality of vertically extending ridges 82d disposed along an outer periphery of an outer surface on an upper side of the thick tube 82b having the attachment opening 82c; and a transition portion 82e disposed between the thin tube 82a and the thick tube 82b. An electrode array section 22e is disposed on the plate 22d inside the thick tube 82b of the dispensing tip 82, and the terminal array section 22f is disposed outside the dispensing tip 82 to form an electrode array plate 22 (refer to FIG. 14).

Figure 14:
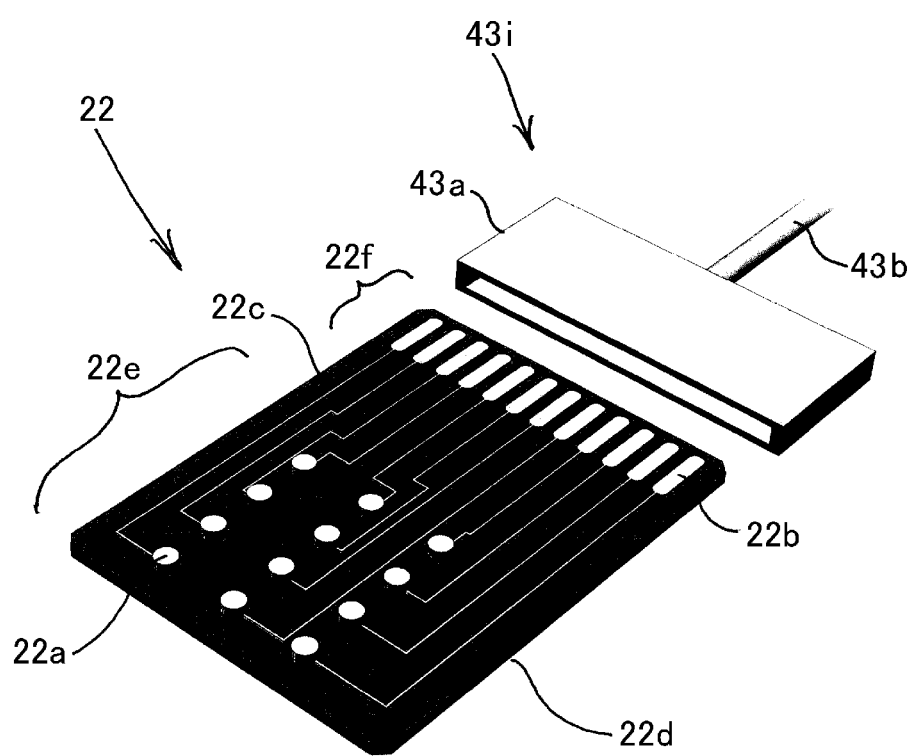
FIG. 14 is an enlarged plan view illustrating an electrode array element illustrated in the device for electrical measurement of a target chemical substance according Third Example illustrated in FIG. 13.

FIG. 14 illustrates the electrode array plate 22 and the plug 43a as the electrode array element support sections $43_1$ to $43_4$.

The electrode array plate 22 includes: the plate 22d formed of an insulator such as glass, ceramic, or resin as a part of a base; one or more (12 in this example) electrodes 22a which are disposed on the plate 22d and to each of which a test substance having a bonding property to a target chemical substance in a solution stored in the liquid storing section group 33b or the measurement container 33c is fixed; an electrode array section 22e in which the electrodes 22a are arrayed and which is disposed on one side of the thin plate-shaped plate 22d; one or more (12 in this example) terminals 22b disposed on the thin plate-shaped plate 22d so as to correspond to the electrodes 22a and electrically connected to the electrodes 22a by a conductive wire 22c; and a terminal array section 22f in which the terminals 22b are arrayed and which is disposed on the other side of the thin plate-shaped plate 22d. The electrode array section 22e is disposed in the thick tube 82b such that liquid sucked by the dispensing tip 82 can come into contact with the electrode 22a. The terminal array section 22f is disposed outside the thick tube 82b and is attachable to the plug 43a. Not that a reference numeral 42b at least includes a rod 42b through which a conductor passes. The conductive wire 22c is embedded in the plate 22d or a layered portion covered with or formed of an insulator.

Subsequently, an operation in a case where the device for electrical measurement of a target chemical substance 102 and a method therefor according to Third Example of the present embodiment are applied to detection of a specific food allergen on the display obligation 7 items (egg, milk, wheat, buckwheat, peanut, shrimp, and a crab) for four kinds of foods will be described with reference to FIG. 13.

The tip and the like storing section group 33a stores the electrode array elements $22_1$ to $22_4$ and the piercing tip with the attachment opening 82c facing upward such that the electrode array elements $22_1$ to $22_4$ and the piercing tip can be supported by being attached to the nozzles and the plugs 42a as the electrode array element support section or only to the nozzles.

Two of the twelve electrodes of the electrode array elements $22_1$ to $22_4$ are electrodes for negative control and positive control. The electrode for negative control is blocked such that an antigen or an antibody is not bonded to the electrode. The electrode for positive control necessarily generates a predetermined electric signal. An antibody (for example, an anti-wheat antibody or an anti-egg antibody) capable of capturing an allergen is fixed to each electrode. Furthermore, each liquid storing section of the liquid storing section group 31b includes, in advance, in order, two sets of a liquid storing section storing 100 µL of a food extract solution extracted from food and three liquid storing sections each storing 200 µL of cleaning buffer solution (1×PBS 0.05% Tween). Note that an antigen in each food extract solution is labeled in advance by bonding the antigen to an electrochemically active substance such as a metal complex via an amino group, a carboxyl group, or the like included in the antigen.

In step S31, the processing head moving mechanism 52 moves the processing head 7 in the Y-axis direction, and moves the processing head 7 above a first storing section (electrode array element storing section) of the tip and the like storing section group 33a storing the electrode array elements $22_1$ to $22_4$. By lowering the four nozzles disposed in the processing head 7 by the Z-axis moving mechanism 53, attachment openings of the electrode array elements $22_1$ to $22_4$ are fitted with and attached to the nozzles. At the same time, the terminal array section 22f of the electrode array plate 22 is attached to each of the plugs $43_1$ to $43_4$.

In step S32, the Z-axis moving mechanism 53 raises the nozzles 83a and the electrode array elements $22_1$ to $22_4$ in the Z-axis direction. Thereafter, the processing head moving mechanism 52 moves the nozzles 83a and the electrode array elements $22_1$ to $22_4$ in the Y-axis direction above the liquid storing section 33b storing the food extract solution. The Z-axis moving mechanism 53 lowers the electrode array elements $22_1$ to $22_4$ supported by the nozzles such that a mouth portion 82f at a tip end of each of the electrode array elements $22_1$ to $22_4$ is inserted into the food extract solution. The suction and discharge mechanism 83 repeatedly sucks and discharges the food extract solution. Suction is performed until reaching such a capacity that the electrode array section 22e of the electrode array plate 22 is immersed in the food extract solution to bring the electrodes 22a into contact with the food extract solution efficiently.

In step S33, the Z-axis moving mechanism 53 raises the electrode array elements $22_1$ to $22_4$ in the Z-axis direction. Thereafter, the processing head moving mechanism 52 moves the electrode array elements $22_1$ to $22_4$ in the Y-axis direction above the liquid storing section 33b storing a cleaning liquid. The Z-axis moving mechanism 53 lowers the electrode array elements $22_1$ to $22_4$. By repeating suction and discharge by the suction and discharge mechanism 83, cleaning is performed. Similarly, cleaning is repeated with respect to other cleaning liquids.

In step S34, the processing head moving mechanism 52 moves the electrode array elements $22_1$ to $22_4$ in the Y-axis direction above the measurement container 33c. The Z-axis moving mechanism 53 lowers the electrode array elements $22_1$ to $22_4$. Thereafter, the suction and discharge mechanism 83 sucks a solution stored in the measurement container 33c. While the mouth portion 82f is immersed in the solution, the applying units $62_1$ to $62_4$ apply a voltage to an antibody bonding to the electrode via the counter electrode 63, and the measurement sections $64_1$ to $64_4$ measure the amount of the voltage. The measurement result is digitally converted, is then stored in a storage unit in the CPU+program+memory 9, and is analyzed by the analysis unit 93.

According to the device for electrical measurement of a target chemical substance and a method therefor according to the present Example, an electrode array element can be automatically attached to each nozzle (electrode array element support section). Therefore, contact with the electrode array element and a dispensing tip by a user can be prevented, and highly reliable processing without cross contamination can be performed. In addition, contact between each electrode of the electrode array element and liquid can be reliably performed by repeatedly sucking and discharging liquid. Therefore, efficiency and rapidity of the processing are high. Furthermore, all processing from liquid dispensing to measurement can be performed using an electrical mechanism. Therefore, it is not necessary to dispose an optical mechanism, and manufacturing can be performed compactly and easily, thereby inexpensively. Furthermore, according to the present Example, although the electrode array section is disposed so as to be able to come into contact with liquid sucked in the thick tube, the terminal array section and the plug are disposed outside the thick tube. Therefore, the terminal array section or the plug does not come into contact with the liquid, short circuit between electrodes can be prevented reliably, and highly reliable processing can be performed.

The above-described embodiments have been described specifically for the purpose of better understanding of the present invention, and do not limit another embodiment. Therefore, the above-described embodiments can be changed within a range not changing the gist of the invention. For example, the above-described Examples have described that the processing head and the electrode array element support section move with respect to the container group. However, the container group may move while the processing head and the electrode array element support section are stationary.

In addition, the numerical values, the number of times, the shape, the number, the amount, and the like used in the above description are not limited to these cases. For example, only the case where the cartridge containers of the container group, the electrode array elements, and the nozzles are arrayed in four rows has been described. However, it is needless to say that the present invention is not limited to this case. In addition, only the case where the number of electrodes or terminals of the electrode array element is 12 has been described. However, it is needless to say that the number of electrodes or terminals is not limited to this case.

Furthermore, only the case where measurement is performed by performing labeling with an intercalating agent or a metal complex has been described. However, measurement can be performed by, for example, an alternating current impedance method without performing labeling.

The devices described in Examples of the present invention, components forming these devices, devices for forming these components, reagents, and the like can be appropriately selected, can be appropriately modified, and can be mutually combined. Presence or absence of an antigen of each subject can be tested using, for example, an electrode array element, a dispensing element (dispensing tip and deformable dispensing tip), an electrode array element support section, a container group, a tip and the like storing section group, a cartridge container, a liquid storing section group, a measurement container or the like, a processing head, a support section moving mechanism, a measurement section, or the like. Alternatively, for example, in a case where a test in a serum solution is performed, presence or absence of an antigen of each subject can be tested by concentrating the serum solution using magnetic particles and fixing an antibody corresponding to each particle for use.

In addition, for the electrode array element described in each of the above Examples, only the case where the electrodes and the terminals are arrayed on a plate-shaped base or a substrate has been described. However, it is needless to say that a case where electrodes and terminals are arrayed on an inner wall of a cylindrical or tubular base is included within the scope of the gist of the present invention.

Incidentally, in the present application, a spatial expression such as "X-axis", "Y-axis", "Z-axis", "above", "below", "inside", "outside", "up and down", "line", or "row" is only for illustrative purposes, and does not limit a particular spatial direction or arrangement of the structure.

INDUSTRIAL APPLICABILITY

The present invention relates to a device for electrical measurement of a target chemical substance, and a method therefor, performs a test of a specimen collected from a patient or the like, and measurement thereof, and can be used particularly in a field requiring handling of a biopolymer such as a gene, an immune system, an amino acid, a protein, or a sugar, and a low molecular biological substance, for example, in various fields such a biochemistry field, an industrial field, an agriculture field such as food, agriculture, or fishery processing, a pharmaceutical field, and a medical field such as hygiene, health, immunity, diseases, or genetics.

REFERENCE SIGNS LIST

10, 101, 102 Device for electrical measurement of target chemical substance $2_1$ to $2_n$, $21_1$ to $21_4$, $22_1$ to $22_4$, $23_1$ to $23_4$ Electrode array element
21e, 22e, 23e Electrode array section
21a, 22a, 23a Electrode
21f, 22f, 23f Terminal array section
21b, 22b, 23b Terminal
21c, 22c, 23c Conductive wire
21d, 23d Base
22d Plate
22 Electrode array plate
3, 31, 32, 33 Container group
$3_1$ to $3_n$ Storing section group
$31_1$, $32_1$ to $32_4$, $33_1$ to $33_4$ Cartridge container
4, 41 Array element support
$4_1$ to $4_n$, $41_1$ to $41_4$, $42_1$ to $42_4$, $43_1$ to $43_4$ Electrode array element support section
5(52, 53) Moving mechanism
7, 71, 72, 73 Processing head
$8_1$ to $8_n$, $81_1$ to $81_n$ Dispensing tip
82 Base (dispensing tip)
9 CPU+program+memory
15, 16, 151 to 156 Non-wetted electrode for application of external electric field

The invention claimed is:

1. A device for electrical measurement of a target chemical substance, comprising:
   one or more electrode array elements each including a base, an electrode array section in which one or more electrodes are disposed on the base and to each of which a test substance is fixed, the test substance having a bonding property to a target chemical substance, and a terminal array section in which one or more terminals disposed on the base so as to correspond to the electrodes and electrically connected to the electrodes are arrayed;
   a processing head including one or more electrode array element support sections supporting the electrode array elements detachably to make electrical connection to the terminals possible;
   a container group including one or more liquid storing sections for of storing liquid, and one or more measurement containers for receiving the target chemical substance and for receiving the electrode array section of an electrode array element;
   a support section moving mechanism for relatively moving the one or more electrode array element support sections with respect to the container group such that the test substance fixed to one or more electrodes of the electrodes array section encounters the target chemical substance; and
   a measurement section capable of measuring a signal generated by applying a predetermined voltage to the test substance fixed to the one or more electrodes of the electrode array section when the electrode array section is received in the measurement containers,
   wherein the container group includes one or more electrode array element storing sections for of storing the electrode array elements such that the electrode array elements are supported by the electrode array element support sections due to the support section moving mechanism.

2. The device for electrical measurement of a target chemical substance according to claim 1, wherein
   the base is formed in a plate shape having a predetermined height, a predetermined width, and a predetermined thickness shorter than the predetermined height and the predetermined width,
   the electrode array element support section includes a plug detachably attached to the terminal array section formed on an upper side of the base and electrically connectable to the terminals of the terminal array section, and
   the container group includes a liquid storing section or a measurement container having a longer inner width than the predetermined width of the base and an inner depth longer than the predetermined thickness but shorter than the predetermined width.

3. The device for electrical measurement of a target chemical substance according to claim 1, wherein
   the processing head further includes a suction and discharge mechanism for sucking and discharging gas, and
   the electrode array element support section includes a dispensing element support section detachably supporting a dispensing element capable of sucking and discharging liquid through a mouth portion at a lower end due to the suction and discharge mechanism, and a plug detachably attached to the terminal array section of the electrode array element and electrically connected to the terminals.

4. The device for electrical measurement of a target chemical substance according to claim 3, wherein the base of the electrode array element includes the dispensing element, the electrode array section is disposed inside the dispensing element, and the terminal array section is disposed inside the dispensing element so as to be located above the electrode array section or is disposed outside the dispensing element.

5. The device for electrical measurement of a target chemical substance according to claim 3, wherein the dispensing element is a dispensing tip, the dispensing element support section includes a nozzle communicating with a suction and discharge mechanism for sucking and discharging gas, the dispensing tip is supported by being detachably attached to the nozzle through an attachment opening at an upper end thereof, the plug is disposed at a tip end of the nozzle such that the electrode array element is located inside the dispensing tip, and the container group further includes a tip storing section for storing the dispensing tip such that the dispensing tip is attachable to the nozzle.

6. The device for electrical measurement of a target chemical substance according to claim 3, wherein the dispensing element includes: a thin tube having the mouth portion; a thick tube communicating with the thin tube; and a storage tube communicating with the thick tube, the electrode array section is disposed in the thick tube, and the storage tube is disposed so as to have a capacity capable of storing all the liquid introduced into the thick tube from the mouth portion.

7. The device for electrical measurement of a target chemical substance according to claim 3, wherein the processing head includes a magnetic force mechanism capable of applying a magnetic force to an inside of the attached dispensing element and removing the magnetic force therefrom and/or a temperature raising and lowering body for raising and lowering a temperature according to a signal from an outside, disposed so as to be close to or be able to approach an outside of the dispensing element or the electrode array element attached to the processing head, and the magnetic force mechanism and/or the temperature raising and lowering body are controlled by a control section.

8. The device for electrical measurement of a target chemical substance according to claim 1, wherein two non-wetted electrodes for application of an external electric field are disposed in the measurement container or the liquid storing section so as to sandwich an inside of the measurement container or an inside of the liquid storing section such that an electric field can be externally applied to the inside of the measurement container or the liquid storing section while the non-wetted electrodes are not in contact with liquid stored in the measurement container or the liquid storing section.

9. The device for electrical measurement of a target chemical substance according to claim 8, wherein the processing head includes a magnetic force mechanism capable of applying a magnetic force to an inside of the attached dispensing element and removing the magnetic force therefrom and/or a temperature raising and lowering body for raising and lowering a temperature according to a signal from an outside, disposed so as to be close to or be able to approach an outside of the dispensing element or the electrode array element attached to the processing head, and the magnetic force mechanism and/or the temperature raising and lowering body are controlled by a control section.

* * * * *